US010071077B2

(12) United States Patent
Beute

(10) Patent No.: US 10,071,077 B2
(45) Date of Patent: Sep. 11, 2018

(54) USE OF ENOXIMONE IN THE TREATMENT OF ATOPIC IMMUNE-RELATED DISORDERS, IN PHARMACEUTICAL COMPOSITION AS WELL AS IN PHARMACEUTICAL PREPARATION

(71) Applicant: BREAKTHROUGH MEDICAL RESEARCH B.V., Almere (NL)

(72) Inventor: Jan Beute, Almere (NL)

(73) Assignee: BREAKTHROUGH MEDICAL RESEARCH B.V., Almere (NL)

( * ) Notice: Subject to any disclaimer, the term of this patent is extended or adjusted under 35 U.S.C. 154(b) by 0 days.

(21) Appl. No.: 15/303,971

(22) PCT Filed: Apr. 14, 2015

(86) PCT No.: PCT/NL2015/050246
§ 371 (c)(1),
(2) Date: Oct. 13, 2016

(87) PCT Pub. No.: WO2015/160249
PCT Pub. Date: Oct. 22, 2015

(65) Prior Publication Data
US 2017/0035735 A1    Feb. 9, 2017

(30) Foreign Application Priority Data
Apr. 14, 2014  (NL) .................... 2012612

(51) Int. Cl.
*A61K 31/4174*   (2006.01)
*C12N 9/16*      (2006.01)
(52) U.S. Cl.
CPC ........... *A61K 31/4174* (2013.01); *C12N 9/16* (2013.01); *C12Y 301/00* (2013.01)
(58) Field of Classification Search
CPC ..... A61K 31/4174; C12Y 301/00; C12N 9/16
See application file for complete search history.

(56) References Cited

U.S. PATENT DOCUMENTS

2006/0292213 A1* 12/2006 Gerber ............... A61K 31/4166
                                                       424/451

FOREIGN PATENT DOCUMENTS

EP    2581082 A1    4/2013
WO    2002/051502 A1    4/2002
WO    2006/007213 A1    1/2006

OTHER PUBLICATIONS

International Search Report of PCT/NL2015/050246 dated Oct. 19, 2015.
Bardin, P., et al., "Effect of Selective Phosphodiesterase 3 Inhibition on the Early and Late Asthmatic Responses to Inhaled Allergen," British Journal of Clinical Pharmacol., vol. 45, pp. 387-391 (Jan. 1, 1998).
Kleinjan, A., et al., "PDE3 Inhibition as Life-Saving Emergency Medication or Life-Threatening Asthma in Human and Suppresses Allergic Airway Inflammation in a House Dust Mite Asthma Mouse Model," Allergy European Jouranl of Allergy & Clinical Immunology, Vol. 69, Suppl. 99, , pp. 97-98 (Sep. 2014)
Santing, R., et al., "Bronchodilatory and Anti-Inflammatory Properties of Inhaled Selective Phosphodiesterase Inhibitors in a Guinea Pig Model of Allergic Asthma," vol. 429, pp. 335-344 (Oct. 19, 2001).
Clayton, Robert A., et al., "The Effect of Selective Phosphodiesterase Inhibitors, Alone and in Combination, on a Murine Model of Allergic Asthma," Respiratory Research, vol. 5, No. 4, pp. 1-9 (May 5, 2004).
Dage, Richard, C., et al., "Pharmacology of Enoximone," Am J Cardiol., vol. 60, pp. 10C-14C (Aug. 14, 1987).
Metra, Marco., et al., "Effects of Low-Dose Oral Enoximone Administration on Mortality, Morbidity, and Excercise Capacity in Patients with Advanced Heaet Failure: the Randomized, Double-Blind, Placebo-Controlled, Parallel Group Essential Trials," Clinical Research Heart Failure, European Heart Journal, vol. 30, pp. 3015-3026 (Aug. 22, 2009).
Morita, Shigemichi, et al., "Pharmacokinetics of Enoximone After Various Intravenous Administrations to Healthy Volunteers," Journal of Pharmaceutical Sciences, vol. 84, No. 2, pp. 152-157 (Feb. 1995).

* cited by examiner

Primary Examiner — Sudhakar Katakam
(74) Attorney, Agent, or Firm — Polsinelli PC; Christopher M. Cabral

(57) ABSTRACT

The invention involves the use of compounds from the class of aroyl-2H-imidazol-2-ones such as enoximone or a pharmaceutically acceptable salt thereof for modulating the immune system involved in a topic and immune-related disorders. In particular, the invention involves the use of (1,3-dihydro-4-methyl-5-[4-(methylthio)benzoyl]-2H-imidazol-2-on) or a pharmaceutically acceptable salt thereof. The invention also involves a pharmaceutical composition including aroyl-2H-imidazol-2-on or a pharmaceutically acceptable salt thereof in an active quantity for the treatment of a topic and immune-related disorders, by modulating the immune system involved in a topic and immune-related disorders. Preference is especially given to a pharmaceutical composition in a dosage unit of 5, 10 or 20 mg, based on the quantity of the active ingredient.

19 Claims, 7 Drawing Sheets

USE OF ENOXIMONE IN THE TREATMENT OF ATOPIC IMMUNE-RELATED DISORDERS, IN PHARMACEUTICAL COMPOSITION AS WELL AS IN PHARMACEUTICAL PREPARATION

This invention involves aroyl-2H-imidazol-2-on, or a pharmaceutically acceptable salt thereof, and using aroyl-2H-imidazol-2-on or a pharmaceutically acceptable salt thereof, preferably enoximone or a pharmaceutically acceptable salt thereof, for the treatment of atopic and immune-related disorders, preferably by modulating the immune system involved in atopic and immune-related disorders, or for the preparation of a medicament for modulation of the immune system involved in atopic and immune-related disorders.

Some uses of this substance are known art. For example, enoximone is administered intravenously in heart failure.

The invention describes a new use of aroyl-2H-imidazol-2-on, preferably enoximone or a pharmaceutically acceptable salt thereof. Enoximone is a compound that belongs to this group that can be referred to as aroyl-2H-imidazol-2-on. In particular, the invention involves the use of the compound 1,3-dihydro-4-methyl-5-[4-(methylthio)benzoyl]-2H-imidazol-2-on, also referred to as 4-methyl-5-{[4-methyl sulfanyl) phenyl]carbonyl}-2,3-dihydro-1H-imidazol-2-on, or a pharmaceutically acceptable salt thereof. Aroyl-2H-imidazol-2-ones of the invention are preferably 4-aroyl-2H-imidazol-2-ones. Examples of aroyl-2H-imidazol-2-ones are 4-benzoyl-1,3-dihydro-2H-imidazol-2-one; 1,3-dihydro-4-(4-nitrobenzoyl)-2H-imidazol-2-one; 4-benzoyl-1,3-diacetyl-1,3-dihydro-2H-imidazol-2-one; 4-benzoyl-1,3-dihydro-5-(lower alkyl)-2H-imidazol-2-one; 4-benzozyl-1,3-diacetyl-1,3-dihydro-5-methyl-2H-imidazol-2-one, 1,3-dihydro-4-(hydroxybenzoyl)-2H-imidazol-2-one; 1,3-dihydro-4-(hydroxybenzoyl)-5-(lower alkyl)-2H-imidazol-2-one; 1,3-diacetyl-1,3-dihydro-4-(3,4-di m ethylbenzoyl)-2H-imidazol-2-one; 1,3-dihydro-4-(3,4-dihydroxybenzoyl)-2H-imidazol-2-one; 1,3-dihydro-4-methyl-5-(4-nitrobenzoyl)-2H-imidazol-2-one, 4-(3-aminobenzoyl)-1,3-dihydro-2H-imidazol-2-one, 4-(4-aminobenzoyl)-1,3-dihydro-2H-imidazol-2-one, and 4-(4-aminobenzoyl)-1,3-dihydro-5-methyl-2H-imidazol-2-one Hereinafter, the terms "enoximone" and "aroyl-2H-imidazol-2-on" will mainly be used, whereby all specific compounds mentioned above are also referred to.

The invention involves in particular the use of the above-mentioned compound for the treatment of atopic and immune-related disorders. Examples of such disorders that can be treated effectively in accordance with the invention are asthma, COPD, allergies or allergic disorders such as hay fever, allergies to domestic animals, constitutional eczema, allergic rhinitis, food allergies and contact allergies. This is a non-exhaustive list of allergies or allergic disorders which have in common that they trigger production of immunoglobulin E (IgE), and which can be treated effectively using the present invention Surprisingly, the compound (respectively the family of compounds) described in this invention has proven to reduce or even eliminate altogether the symptoms associated with the above-mentioned disorders during a longer period than expected when expectation is based on the compound's residence time in the body. For example, enoximone is metabolised to a less active sulfoxide and subsequently excreted via the kidneys with a half life of approximately 4 hours. Nonetheless, effects of the compound have been observed to last longer than these 4 hours, or longer than multiple series of four hours, even lasting well beyond a month. An explanation for this is that enoximone influences or modulates or exerts an effect on the immune system or could be considered as an immune modulator. An immune modulator is later defined herein. In this invention the effect of aroyl-2H-imidazol-2-on, preferably enoximone, on the behaviour of immune cells is shown, and aroyl-2H-imidazol-2-on, preferably enoximone, is additionally shown to reduce immune cell activity involved in allergic airway inflammation, thus asserting an anti-asthma or anti-allergic effect. The invention therefore also involves the use of an aroyl-2H-imidazol-2-on, particularly the (1,3-dihydro-4-methyl-5-[4-(methylthio)benzoyl]-2H-imidazol-2-on compound or enoximone, or a pharmaceutically acceptable salt thereof, for modulating the immune system of a patient suffering from atopic and immune-related disorders.

Furthermore, the invention involves a pharmaceutical composition containing aroyl-2H-imidazol-2-on, preferably enoximone or any pharmaceutically acceptable salt of either in an active quantity for the treatment of atopic and immune-related disorders.

The use of aroyl-2H-imidazol-2-on, preferably enoximone or any pharmaceutically acceptable salt of either leads to a marked improvement of the quality of life of the patient involved. An additional effect of the use of aroyl-2H-imidazol-2-on, preferably enoximone or a pharmaceutically acceptable salt thereof in accordance with the invention is that this leads to substantially lower costs of the medical treatment of atopic and immune-related disorders.

Where reference is made to the enoximone substance hereinafter, reference is made to any form of enoximone or a pharmaceutically acceptable salt thereof, particularly an aroyl-2H-imidazol-2-on, in particular the (1,3-dihydro-4-methyl-5-[4-(methylthio)benzoyl]-2H-imidazol-2-on) compound or a pharmaceutically acceptable salt thereof.

Characteristics of Asthma, Allergy, Etc.

Bronchial asthma, in all its various forms such as refractory asthma, difficult to treat asthma, stable asthma, acute asthma, corticosteroid-resistant asthma, aggravated asthma as a result of an inflammatory reaction or an allergic reaction (hereinafter referred to as "asthma"), is a chronic inflammation of the airways as a result of hypersensitivity.

Asthma is characterised by difficult breathing, incidental or chronic, as a result of a narrowing of the airways (commonly referred to as "bronchoconstriction"). This is caused by inflammation of the mucosa of the airways, paired with a constriction of the smooth muscle tissue situated under the mucosa; increased production of mucus and oedema in the bronchial mucosa can contribute to the development or exacerbation of asthma.

Asthma is an obstructive airway disease characterized by inflamed airways, structural abnormalities of the airways and physiological abnormalities and shortness of breath (Barnes PJ., Nat. Rev. Immunol. 2008; 8:183-192). There are three typical pathophysiological hallmarks of asthma: bronchial hyper reactivity, eosinophilic airway inflammation and specific IgE formation. In general, eosinophilic airway inflammation most characteristically plays a pathophysiological role and it can easily be used as a marker for allergic airway inflammation (Bousquet J, et al., New Eng. J. Med. 1990; 323:1033-1039).

In addition to the above causes, other factors such as genetic, allergic or environmental factors can be responsible for the development, exacerbation or chronicity of asthma or asthma-related disorders such as COPD. There are indications that asthma can evolve into COPD.

The symptoms, problems or consequences of asthma and COPD can be manifold, ranging from light dyspnoea and disability related to environmental influences or exertions, to a deterioration in condition or even to lasting invalidity, due to the illness itself as well as to the side effects of the treatment.

Allergic disorders or allergies such as hay fever, allergies to domestic animals, constitutional eczema and contact allergies are closely related to asthma. These are caused by hypersensitivity to so-called allergens, which have in common that they trigger production of immunoglobulin E (IgE).

The symptoms of allergic disorders are also manifold, including irritations of the skin and mucosae, skin disorders (both dry and oozing), itching, discolouring of the skin and food intolerance. Allergic disorders are often highly socially charged, which strongly affects the patient's quality of life.

The diagnostic criteria for allergic disorders depend on the allergen involved and how it operates: for instance, the skin can be affected by a contact allergy (such as or e.g. eczema, itching, redness, flakiness); food allergies can lead to skin and gastro-intestinal disorders; airways disorders such as hay fever, irritation of the mucosae and coughing can be brought on by allergens such as pollen, aromas and colouring agents, dust mites, etc. Skin and RAST tests can be indicative in this regard.

In the case of asthma and COPD, the most important diagnostic criteria are the symptoms as described by the patients themselves, a lung function test and the quantity of medication taken corresponding to the degree of response of the patient. Corticosteroids are particularly indicative in this respect. Allergy tests can be performed to determine whether the asthma or COPD is related to specific allergen stimulations. Exertion tests can also be carried out to see if there is a relation with physical exercise.

Together, the above mentioned disorders should be considered as part of a so-called atopic constitution.

Standard Drug Treatment of Asthma, Allergies, Etc.

Asthma and COPD are usually treated with beta-2 agonists as bronchodilators; with parasympatholytics and anticholinergics to counteract bronchoconstriction and bronchospasm and to reduce the production of mucus; with corticosteroids to combat inflammation reactions; with magnesium sulphate for acute attacks; or with aminophyllines as long-lasting weak bronchodilators. Treatment usually involves a combination of the above medicines; administration varies between injections, tablets and atomisation. The administration of oxygen, whether incidentally or chronic, can also be considered.

The effect of bronchodilators is usually observed within a few seconds (i.e. at least 5, 10, 15, 20, 30 seconds when administrated by injection) or a minute or a few minutes (i.e. at least 1, 2, 3, 4, 5 minutes when administrated orally) after inhalation or after intravenous injection (especially in the case of bolus injection) of the active compound as illustrated in Beute J, 2012, Brit. J. Anaesthesia, 112(6): 1105-1108. The duration of the bronchodilator effect may be 2, 3, 4, 5, or 6 hours after the first administration, preferably injection. Usually, the bronchodilator effect is no longer detectable 6 hours after administration, preferably injection.

Allergic disorders are treated with anticholinergics when it concerns irritations of the mucosae, and with various creams, with or without corticosteroids, for skin disorders e.g. In severe cases special baths and even cytostatics may be used. In this regard it is important that the patient should try to avoid or avert the allergens as much as possible.

Effects of Standard Drug Treatment

Many asthma/COPD patients who are treated with the above medicines may seem stable, but nevertheless experience problems or aggravated symptoms during physical exertion because of a reaction to an allergen or due to an (airway) infection unrelated to asthma. Allergy patients experience similar problems when confronted by allergens that are specific to their particular immune system.

Increasing the dose of traditional medication (preferably corticosteroid) does not always lead to a reduction of symptoms, but often rather to aggravation of the side effects of the medication, such as tachycardia when using beta-2 agonists and too much drying of the sputum (dry lungs, irritation of the airways and higher susceptibility to infection) in the case of parasympatholytics and anticholinergics. At high doses, corticosteroids can lead to a wide range of problems, the most common of which are drying of the sputum, increased susceptibility to infection, disrupted wound healing, compromised immunity, muscle degradation, osteoporosis and thinning of the skin. In serious cases, the side effects of the treatment can lead to severe disability, especially due to a decline of the patient's condition and, in the case of allergy patients, due to excoriation of the skin. In general, it can be observed that a high percentage of patients react insufficiently or inadequately to the traditional treatments as described above. The subsequent question is whether to increase the dosage and/or frequency of the medication, but experience has shown that such a change very often does not lead to the desired results. It must be considered that the side effects of such a change can be extremely radical and may well become even more severe than the ailment itself. Furthermore, a heavier medication programme requires a lot of the patient: often expectations are not being fulfilled, which leads to disappointment, and significant schedular constraints are being placed on the patient regarding taking their medication on time, which can have a considerable social impact.

Asthma/COPD patients are currently treated by their GP, a lung specialist or in a special outpatient asthma centre. The treatment consists of maintenance medication for chronic and stable conditions and extra doses for acute attacks. In some cases it is necessary to temporarily or chronically provide the patient with oxygen by means of an oxygen device. It can also prove beneficial or necessary to admit the patient to a special asthma/COPD centre or have them recover in a climate to which asthma/COPD reacts positively. In severe cases, the disease interferes so radically with the patient's life that a normal life is virtually impossible.

Allergy patients are also usually treated by their GP. Severe cases are referred to academic outpatient allergy centres.

Unfortunately, it has been shown that the traditional treatment of allergic disorders is often unable to offer improvement.

It is therefore obvious that the treatment of asthma, COPD and allergic disorders is a challenge both medically and financially. The group of patients is large and varied, and presents many possible options, ranging from mere light maintenance treatments to long term stays abroad, and straining the costs of both the therapeutic and social services budget. Another relevant concern is the substantial loss of productive work time.

Asthma, COPD and allergic disorders will affect the life of the patient at any time, regardless of the severity of the disorder. Particularly when the disorder is present at a young age, severe mental traumas may appear on top of the physical ones.

The traditional treatment as described above is limited for many patients: the medicines have a limited effect or do not or barely or only barely reach the place where they are supposed to work. When no improvement occurs, increasing the dosage is usually ineffective or even impossible due to the many detrimental side effects.

Present Invention

In the present invention enoximone or another aroyl-2H-imidazol-2-on is used for treatment of an atopic and immune-related disorder.

Accordingly, aroyl-2H-imidazol-2-on or a pharmaceutically acceptable salt thereof is in one aspect for use for the treatment of atopic and immune-related disorders, preferably by modulating the immune system involved in atopic and immune-related disorders of the treated subject, preferably wherein said aroyl-2H-imidazol-2-on is enoximone.

In a preferred embodiment, aroyl-2H-imidazol-2-on as defined above is for use, wherein said immune-related disorder is asthma, or preferably chosen from the list of: refractory asthma, difficult-to-treat asthma, stable asthma, acute asthma, corticosteroid-resistant asthma, aggravated asthma as a result of an inflammatory reaction or an allergic reaction, allergy and COPD. Allergy is preferably any allergic disorder wherein IgE is produced such as hay fever, allergies to domestic animals, food allergies, constitutional eczema, allergic rhinitis and contact allergies.

Said treatment can comprise treating or preventing an atopic and immune-related disorder, preferably treating, curing, preventing, stabilizing and/or delaying such a disorder. Aroyl-2H-imidazol-2-on, preferably enoximone is preferably considered as an immune modulator as defined later herein.

In the context of the invention, preventing, treating, curing, stabilizing and/or delaying a disease or condition associated with asthma or with allergy and/or a disease or condition associated with the immune system (i.e. atopic and immune related disorder) and/or a disease or condition being asthma or allergy may mean that:

at least a symptom of this disease or condition has been improved, at least a parameter associated with this disease or condition has been improved.

Depending on the identity of the disease or condition, a symptom may be at least one of the following symptoms:

Itching, red skin and urticarial for (domestic) animal allergy,

Sneezing, nasal blockage, nasal discharge, itching of the nose, itching of the eye and itching of the palate, for allergic rhinitis, Wheezing, dyspnea, coughing, chest tightness, sputum production, and nighttime awakenings for asthma.

The improvement may be measured and/or visible (i.e. significant improvement) after one hour of the onset of the treatment, or 2, 3, 4, 5, 6, 7, 8, 9, 10, 11, 12, 13, 14, 15, 16, 17, 18, 19, 20, 21, 22, 23, 24 hours, or after one day, two days, four days, or after at least one week, one month, six months after the onset of the treatment or more. Preferably the improvement is visible after at least 6 hours, more preferably after at least 12 hours, 24 hours of the onset of the treatment and/or is not the consequence of a bronchodilatation effect.

It is encompassed by the invention that the treatment may consist of the administration of a single dose, or two doses or three doses of the compound.

It is also encompassed by the invention, that the treatment may comprise or consist of an administration frequency of no more often than once per day, or preferably once every four days, or preferably no more often than six, five, four, three, or two times per week, or more preferably no more often than weekly or less often than once per week or each two weeks or each three weeks or monthly or even less frequently.

During the course of the treatment, the symptom may also occur less and less frequently: concept of symptom free day or episode free day. It may mean that a subject may be symptom free for an increasing period of time of at least 1, 2, 3, 4, 5, 6 hour or at least 1, 2, 3, 4, 5, 6 days or at least 1, 2, 3 week with one single, or two or three doses of the compound. As a result a subject may adapt the frequency of administration of enoximone depending on the frequency of occurrence of a symptom. Enoximone may be administrated once or twice a week as a first dose and depending on the evolution of the frequency of the occurrence of a symptom, it may subsequently be administrated every week, subsequently every two weeks.

The immune modulator effect, preferably the anti-asthma or anti-allergic effect is preferably identified in a subject through one of the following parameters/symptoms:

an inhibition of activity or a detectable decrease of activity of a PDE, preferably PDE3 and/or PDE4 and/or an inhibition of activity of cells of the immune system or a detectable decrease of activity of cells of the immune system, such as human peripheral blood mononuclear cells (PBMCs) and/or an inhibition of activity or proliferation of T-cells stimulated with an antigen or an allergen or a detectable decrease of activity or of proliferation of such T-cells, and/or an inhibition of activity or proliferation of eosinophils or a detectable decrease of activity or of proliferation of eosinophils, and/or an inhibition of activity or proliferation of ILC2 cells or a detectable decrease of activity or of proliferation of ILC2 cells, and/or an inhibition of activity or proliferation of dendritic cells or a detectable decrease of activity or of proliferation of dendritic cells and/or an inhibition of activity or proliferation of B cells or a detectable decrease of activity or of proliferation of B cells and/or an inhibition of activity or proliferation of macrophages or a detectable decrease of activity or of proliferation of macrophages, and/or a decrease or reduction of the level of IgE and/or a delay in occurrence of symptoms as experienced by the subject.

A symptom may be assessed by interview or anamnesis, or alternately by known tests that assess condition or fatigue levels as appropriate. When appropriate, a parameter can be considered to be improved or deteriorated on the indication of the subject.

Asthma severity levels are assessed as provided in the British guideline on the Management of Asthma (Guideline No. 101; ISBN 978 1 90581 28 5) and can improve as described in those guidelines.

An activity of cells of the immune system or a detectable decrease of activity of cells of the immune system, such as human peripheral blood mononuclear cells (PBMCs) may encompass the reduction of the production of an inflammatory mediator. Such a mediator may be histamine, leukotrienes or T-helper 2 cytokines.

The assessment of the IgE level may be carried out using techniques known to the skilled person as ELISA.

Proliferation of cells and/or cell viability may be assessed using known techniques such as the MTS assay, or such as FACS techniques as described in the examples. When FACS is used to assess cell proliferation, a detected reduction in eosinophil numbers, or reduced numbers of ILC2s, T-cells and macrophages, can indicate that aroyl-2H-imidazol-2-on, preferably enoximone has an anti-allergic or anti-asthma effect or is an immune modulator. Enzyme expression and/or activity can be assessed using known techniques. Preferably, a decrease or increase of a parameter to be assessed means a change of at least 5% of the value corresponding to that parameter. More preferably, a decrease or increase of the value means a change of at least 10%, even more preferably at least 20%, at least 30%, at least 40%, at least 50%, at least 70%, at least 90%, or 100%. In this latter case, it can be the case that there is no longer a detectable value associated with the parameter.

Preferably, a PBMC proliferation assay is performed as follows: PBMCs obtained from buffy coats are preferably isolated by using Ficoll-Paque (density 1.077 g/cm$^3$) density gradient centrifugation. After washing, cells are preferably frozen via a cool down procedure by admixing with dimethyl sulfoxide (DMSO, final concentration 10%) and gradually cooled till minus 80° C. and stored in minus 180° C. until use. Stored PBMCs are thawed and washed 2 times with RPMI containing 10% heat-inactivated fetal bovine serum, gentamycine and β-mercaptoethanol, labelled with Carboxyfluorescein succinimidyl ester (CF SE) and seeded at $10^5$ cells or $2\times10^5$ cells or $3\times10^5$ cells/well in 96 round bottom wells plates in the presence of tetanus toxoid (3Lf/ml, RIVM, Bilthoven, The Netherlands). Cells are cultured in the presence of diluent or aroyl-2H-imidazol-2-on, preferably enoximone 25 µg/ml. Cells are harvested and quantified by Fluorescence-activated cell sorting (FACS) (CD3, CD4 and CD14 and CD19) after 7-13 days. Proportions of divided and undivided CD4 cells are quantified. An effect of aroyl-2H-imidazol-2-on, preferably enoximone on human PBMC proliferation induced by the stimulation with tetanus toxoid is preferably reduction of CD4 positive T-cells. This indicates a direct effect of enoximone on tetanus toxoid-induced T-cell proliferation and can be considered an immune modulatory effect.

Preferably, immunohistochemical staining to detect enzyme expression are performed as follows: in a half-automatic stainer (Sequenza), using acetone-fixed slides washed with PBS and incubated and blocked in diluted normal goat serum (CLB, Amsterdam, the Netherlands). Sections are preferably stained with mouse anti human PDE3A (clone 2D7 Abnova), mouse anti human PDE3B (clone F-9 Santa Cruz Biotechnology) or rabbit anti human PDE4. The primary antibody is preferably detected using goat anti mouse long-chain biotinstreptavidin conjugated-alkaline phosphatase (BioGenix) or with goat anti rabbit conjugated-alkaline phosphatase (Sigma). After rinsing, slides are preferably incubated with New Fuchsin substrate. Finally, the sections are preferably counterstained with Gills triple strength haematoxylin and mounted in Vecta Mount (Vector).

In the present invention it is demonstrated that enoximone can be used as an inhibitor of the enzyme class of phosphodiesterases (PDEs), which comprises PDE3 and PDE4 (see example 4, especially FIG. 1). These two enzymes are expressed in structural cells of the airways and cells of the immune system. Human smooth muscle cells, epithelial cells and endothelial cells further express PDE3. We surprisingly observed that PDE3 inhibition with enoximone abrogates eosinophilic airway inflammation in an in vivo house dust mite driven mouse model for allergy (see example 4). Human peripheral blood mononuclear cells (PBMCs) in vitro stimulated with tetanus toxoid showed a diminished T-cell proliferation when treated with enoximone.

In a preferred embodiment, the present invention provides a new indication or a new medical use for aroyl-2H-imidazol-2-on, preferably for the substance enoximone, which can be used for asthma, COPD, allergy and other atopic and/or immune-related disorders, with direct as well as long term maintenance results.

Allergy could be replaced by allergy or allergic disorders wherein IgE is produced such as hay fever, allergies to domestic animals, constitutional eczema, food allergies, allergic rhinitis and contact allergies, A long term maintenance result can be the improvement of a parameter or a symptom associated with a condition related to atopic and immune-related disorders (i.e. immune modulator) such as asthma or allergy as defined herein, said improvement lasting for at least a period of time that is longer than the expected residency of aroyl-2H-imidazol-2-on, preferably enoximone in the body.

For example, when said disorder is asthma, a long term maintenance result can be the absence of difficulty of breathing for at least a week, two weeks, three weeks, a month, two months, three months, four months after administration of a single dose or two doses or three doses of aroyl-2H-imidazol-2-on, preferably enoximone.

Breathing may be assessed by the respiratory minute volume. Blood gas values and respiratory minute values may be assessed using known techniques. A value may be considered to be improved at the judgement of a treating physician, or when a change of at least 1% has been observed.

For example, when said disorder is allergy, a long term maintenance result can be the absence of or improvement of a parameter of symptom associated with allergy for at least 1, 2, 3, 4, 5, 6, 7, day or a week, two weeks, three weeks, a month, two months, three months, four months after administration of a single dose or two doses or three doses of aroyl-2H-imidazol-2-on, preferably enoximone. A preferred symptom associated with or symptom of allergy has already been defined herein.

As such, long term maintenance results of aroyl-2H-imidazol-2-on, preferably enoximone are preferably based on its effects on the immune system, or in other words on the fact that aroyl-2H-imidazol-2-on, preferably enoximone modulates the immune system (i.e. immune modulator).

A long term maintenance result can be the improvement of a parameter or a symptom associated with a condition related to atopic and immune-related disorders (i.e. immune modulator) such as asthma or allergy as defined herein, wherein said improvement:
  a) is preferably not seen within a few or within 5, 10, 15, 20, 30 seconds or one minute or a few or 1, 2, 3, 4 or 5 minutes after aroyl-2H-imidazol-2-on (preferably enoximone) has been administrated or after the single dose of such compound has been administrated or after the first dose of such compound has been administrated and/or,
  b) is preferably seen within at least 1, 2, 3, 4, 5, 6, 7, 8, 9, 10, 11, 12, 13, 14, 15, 16, 17, 18, 19, 20, 21, 22, 23, 24 hours, more preferably at least 6, 7, 8, 9, 10 hours after such compound has been administrated or after the single dose of such compound has been administrated or after the first dose of such compound has been administrated, and/or
- c) has preferably a duration of at least 4, 5, 6, 7, 8, 9, 10, 11, 12, 13, 14, 15, 16, 17, 18, 19, 20, 21, 22, 23, 24 hours, or at least 1, 2, 3, 4, 5, 6, 7 days or 1, 2, 3, 4, 5, 6 weeks after such compound has been administrated or after the single dose of such compound has been administrated or after the first dose of such compound has been administrated, and/or
- d) is preferably not seen within a few or within 5, 10, 15, 20, 30 seconds or one minute or a few or 1, 2, 3, 4, 5 minutes after such compound has been administrated or after two or three doses of such compound has been administrated, and/or
- e) is preferably seen within at least 1, 2, 3, 4, 5, 6, 7, 8, 9, 10, 11, 12, 13, 14, 15, 16, 17, 18, 19, 20, 21, 22, 23, 24 hours, more preferably at least 6, 7, 8, 9, 10 hours after two or three dose of such compound has been administrated and/or
- f)) has preferably a duration of at least 4, 5, 6, 7, 8, 9, 10, 11, 12, 13, 14, 15, 16, 17, 18, 19, 20, 21, 22, 23, 24 hours, or at least 1, 2, 3, 4, 5, 6, 7 days or 1, 2, 3, 4, 5, 6 weeks after two or three dose of such compound has been administrated.

Accordingly, in a preferred embodiment, aroyl-2H-imidazol-2-on is for modulating the immune system of the treated subject wherein an improvement of a parameter or a symptom associated with said disorder is
- a) is not seen within 10, 15, 20, 30 seconds or within 1 minute after such compound has been administrated or after the single dose of such compound has been administrated or after the first dose of such compound has been administrated and/or
- b) is seen within at least 1 hour, more preferably at least 6 hours after such compound has been administrated or after the single dose of such compound has been administrated or after the first dose of such compound has been administrated and/or
- c) has a duration of at least 4 hours, or at least 1 day after such compound has been administrated or after the single dose of such compound has been administrated or after the first dose of such compound has been administrated.

A long term maintenance result can also be the absence of a parameter or a symptom associated with a condition related to atopic and immune-related disorders (i.e. immune modulator) such as asthma or allergy as defined herein, wherein said absence:
- a) is preferably not seen within a few or within 5, 10, 15, 20 or 30 seconds or one minute or a few or 1, 2, 3, 4, 5 minutes after such compound has been administrated or after the single dose of such compound has been administrated or after the first dose of such compound has been administrated and/or,
- b) is preferably seen within at least 1, 2, 3, 4, 5, 6, 7, 8, 9, 10, 11, 12, 13, 14, 15, 16, 17, 18, 19, 20, 21, 22, 23, 24 hours, more preferably at least 6, 7, 8, 9, 10 hours after such compound has been administrated or after the single dose of such compound has been administrated or after the first dose of such compound has been administrated,
and/or
- c) has preferably a duration of at least 4, 5, 6, 7, 8, 9, 10, 11, 12, 13, 14, 15, 16, 17, 18, 19, 20, 21, 22, 23, 24 hours, or at least 1, 2, 3, 4, 5, 6, 7 days or 1, 2, 3, 4, 5, 6 weeks after such compound has been administrated or after the single dose of such compound has been administrated or after the first dose of such compound has been administrated, and/or
- d) is preferably not seen within a few or 5, 10, 15, 20 or 30 seconds or one minute or a few or 1, 2, 3, 4 or 5 minutes after such compound has been administrated or after two or three doses of such compound has been administrated, and/or
- e) is preferably seen within at least 1, 2, 3, 4, 5, 6, 7, 8, 9, 10, 11, 12, 13, 14, 15, 16, 17, 18, 19, 20, 21, 22, 23, 24 hours, more preferably at least 6, 7, 8, 9, 10 hours after two or three dose of such compound has been administrated and/or
- f)) has preferably a duration of at least 4, 5, 6, 7, 8, 9, 10, 11, 12, 13, 14, 15, 16, 17, 18, 19, 20, 21, 22, 23, 24 hours, or at least 1, 2, 3, 4, 5, 6, 7 days or 1, 2, 3, 4, 5, 6 weeks after two or three dose of such compound has been administrated.

Accordingly aroyl-2H-imidazol-2-on as defined herein is in one preferred embodiment for use for modulating the immune system of the treated subject wherein an improvement of a parameter or a symptom associated with said disorder is visible for:
- a) a period of time which is longer than the expected residency of said Aroyl-2H-imidazol-2-on and/or
- b) at least one week after administration of said Aroyl-2H-imidazol-2-on.

In particular, the present invention relates to the use of aroyl-2H-imidazol-2-on preferably enoximone as oral medication (solid or fluid), inhalation medication, topical medication, suppository or vaginal tablet or injectable medium, for example with delayed release, for the treatment of asthma, COPD and atopic and immune-related disorders, included but not limited to refractory asthma, difficult-to-treat asthma, corticosteroid-resistant asthma, chronic asthma, stable asthma, acute asthma, temporarily aggravated asthma, COPD and more generally immune-related and allergic conditions (i.e. allergy or allergic disorders wherein IgE is produced such as hay fever, allergies to domestic animals, food allergies, constitutional eczema, allergic rhinitis and contact allergies) including but not limited to hay fever, dust mite allergy and allergy to dogs, cats, rabbits and horses. In these disorders enoximone can be used as the primary as well as an adjuvant drug or as a further additional drug. The novelty here is that enoximone acts on the immunology of atopic and immune-related disorders. It effectuates a modulation of the immune system and is seen as an immune modulator as earlier defined herein.

Subjects with asthma or allergic disorders wherein IgE is produced such as hay fever, allergies to domestic animals, constitutional eczema, allergic rhinitis and contact allergies or related immune-related disorders can benefit from both the bronchodilating effect of aroyl-2H-imidazol-2-on, preferably enoximone as well as from its modulation of the immune system, for example as an inhibitor of the enzyme class of phosphodiesterases (PDEs). These indications function through different mechanisms. The bronchodilation can in such a case be seen as a palliative treatment of the immediate symptoms, while the immunomodulation such as the PDE inhibition can be seen as a treatment of the cause of the symptoms, which can have a lasting and durable effect by preventing future attacks or symptoms.

Subjects with immune-related disorders do not necessarily experience a benefit from the bronchodilating effect of aroyl-2H-imidazol-2-on, preferably enoximone. The immune modulating effect of the compound may be the primary effect for these subjects. In this context, the immune-related disorder is allergic rhinitis or hay fever or eczema or contact allergies wherein no bronchodilation is needed. In an embodiment of the invention, aroyl-2H-imidazol-2-on, preferably enoximone or a composition comprising aroyl-2H-imidazol-2-on, preferably enoximone is used for preventing, delaying, ameliorating and/or treating an immune-related disorder in a subject, wherein said subject is preferably not afflicted by asthma, and preferably not afflicted by refractory asthma, difficult-to-treat asthma, stable asthma, acute asthma, aggravated asthma as a result of an inflammatory reaction, or COPD. In an embodiment of the invention, the bronchodilating effect of aroyl-2H-imidazol-2-on, preferably enoximone is not the effect encompassed by the present invention. In an embodiment of the invention, aroyl-2H-imidazol-2-on, preferably enoximone is used for preventing, delaying, ameliorating and/or treating a disease or condition in a subject, wherein said disease or condition is preferably asthma, more preferably refractory asthma, difficult-to-treat asthma, stable asthma, acute asthma, aggravated asthma as a result of an inflammatory reaction, or COPD, allergy or allergic disorders wherein IgE is produced such as hay fever, allergies to domestic animals, constitutional eczema, eczema, food allergies, allergic rhinitis and contact allergies, wherein said use is not for achieving bronchodilation or immediate bronchodilation. Preferably, in such a case a long-lasting effect is achieved. Quantification of bronchodilation or of immediate bronchiodilation may be carried out using Peak Respiratory Flow after 10 seconds or after 30 seconds after enoximone has been administrated. Subjects can be afflicted simultaneously both by asthma and by other immune-related disorders. These subjects can benefit from the known bronchodilating indication as well as from the new indications that aroyl-2H-imidazol-2-on, preferably enoximone can be used as an inhibitor of the enzyme class of phosphodiesterases (PDEs) and/or that aroyl-2H-imidazol-2-on, preferably enoximone can modulate the immune system. This makes different mechanisms of action of aroyl-2H-imidazol-2-on, preferably enoximone relevant for these subjects.

Related to the description above, an embodiment of the invention is the use of aroyl-2H-imidazol-2-on, preferably enoximone as a PDE (preferably PDE3 and/or PDE4) inhibitor for preventing, delaying, ameliorating and/or treating a disease or condition in a subject, wherein said disease or condition is preferably asthma, more preferably refractory asthma, difficult-to-treat asthma, stable asthma, acute asthma, corticosteroid-resistant asthma, aggravated asthma as a result of an inflammatory reaction, or COPD, allergies or allergic disorders wherein IgE is produced such as hay fever, allergies to domestic animals, food allergies, constitutional eczema, eczema, allergic rhinitis and contact allergies, preferably wherein said use is not for achieving bronchiodilatation or not for achieving immediate bronchodilation.

The multiple mechanisms of action allow aroyl-2H-imidazol-2-on, preferably enoximone to be used for the treatment of subjects that do not respond to certain other forms of treatment. In an embodiment of the invention, aroyl-2H-imidazol-2-on is used for the treatment of atopic and immune-related disorders in subjects that show limited or no response to treatment with at least one of the following: beta-2 agonists, parasympatholytics, anticholinergics, aminophyllines, magnesium sulphate, corticosteroids and cytostatics.

Accordingly, aroyl-2H-imidazol-2-on as defined herein is in one preferred embodiment for use for modulating the immune system of the treated subject wherein an improvement of a parameter or a symptom associated with said disorder is not visible within a few seconds or a few minutes after administration of said Aroyl-2H-imidazol-2-on. In this context "few" means at least 1, 5, 10, 20 or more.

Accordingly a Aroyl-2H-imidazol-2-on as defined herein is in one preferred embodiment for use for modulating the immune system of the treated subject wherein said aroyl-2H-imidazol-2-on is administrated no more often than once per day, or preferably once every four days, or preferably no more often than six, five, four, three, or two times per week, or more preferably no more often than weekly or less often than once per week or each two weeks or each three weeks or monthly or even less frequently.

Accordingly aroyl-2H-imidazol-2-on as defined herein is in one preferred embodiment for use for modulating the immune system of the treated subject wherein said aroyl-2H-imidazol-2-on does not or does no longer achieve or induce bronchiodilatation.

Form of the Substance

According to the present invention, aroyl-2H-imidazol-2-on, preferably enoximone is a solid substance which can for example be processed into tablets, suppositories, enemas, vaginal tablets, suspensions, powders, (transdermal) patches and creams. In the above forms, the patients can manage the intake or application themselves, obviously in accordance with the prescriptions of the treating physician. An injectable preparation (subcutaneous, intracutaneous or intramuscular), for example a depot preparation with delayed release, is another possible form. This can be administered in an outpatient centre or by a GP or physician. Unlike the existing form of administration consisting of a fluid, dissolved through a special procedure (corresponding use in heart failure), which must always be administered in a clinical situation, these forms of application are new and much more accessible.

In an embodiment, aroyl-2H-imidazol-2-on, preferably enoximone is not injected intravenously, more preferably not injected via a bolus injection.

Form of Administration and Quantity

According to the present invention, the active substance aroyl-2H-imidazol-2-on, preferably enoximone can be taken both as a fluid and as a solid and can also be applied to the skin. The fluid oral form of administration is a suspension. The possible solid oral forms are dispersible tablets, effervescent tablets, coated tablets (capsules or granules), delayed release tablets or modified release tablets (capsules or granules) (slow release), liquid soft gel capsules, gums or chewing gums, sublingual preparations, capsules, powders, granules, patches, enemas, tablets, preferably vaginal tablets, suppositories or creams or ointment, oral solutions, oral suspensions. Preferred tablet or capsule formulations are provided in examples 5, 6, 7 or 8.

An injectable depot preparation (sub/intracutaneous or intramuscular) is also conceivable. Enoximone may also be formulated into a soap, cream, shower gel/cream and/or shampoo (topical use).

The medicine is also suitable for use as inhalation powder or aqueous suspension for inhalation (see example 9). Where a uniform distribution of the medicine is required, adjuvants and/or carrier substances and/or other excipients can be added, known to the market.

These substances must be compatible with the active substance.

The solid version of the medication can be taken in an advantageous manner with a fluid or a solid and/or other excipients.

The fluid version can be mixed with or dispersed in a fluid in an advantageous manner and/or other excipients.

The inhalation version is administered directly with an inhalator as a solid or a fluid, or optionally in combination with a carrier and/or other excipients.

The suspension version contains enoximone mixed with a compatible fluid and/or other excipients.

For the cream version, enoximone can be added to a dermatological medium in a solid or fluid form, possibly containing further excipients.

Sublingual preparation is attractive as it exhibits a quick resorption (i.e. less than 60 s) and it is unobstructive. Gum or chewing preparation is attractive especially for children as it is not perceived as a drug or medicament. It is also not obstructive.

Enoximone may also be formulated to be administered as a soap, cream, shower gel/cream and/or shampoo. This is especially attractive for eczema patients. They often are very allergic or tender to normal soaps and shampoos.

When enoximone is administered orally, it is preferable that the quantity of active substance is situated in a range from 0.01 to 2 mg per kg body weight, preferably 0.01 to 0.8 mg/kg, preferably 0.01 to 8 mg/kg, preferably at least 0.05 mg/kg, more preferably at least 0.1 mg/kg, even more preferably at least 0.2 mg/kg and most preferably at least 0.25 mg/kg. Furthermore, the quantity is preferably at most 1.5 mg/kg, more preferably at most 1 mg/kg, even more preferably at most 0.8 mg/kg and most preferably at most 0.5 mg/kg. The maximum daily dose of the active substance is preferably 2 mg/kg of body weight yet at most 250 mg/kg body weight, more preferably at most 200 mg/kg body weight, even more preferably at most 150 mg/kg body weight.

The solid form of administration can for example be made available in dosage units of 5, 10 and 20 mg, relative to the quantity of aroyl-2H-imidazol-2-on, preferably enoximone.

When aroyl-2H-imidazol-2-on, preferably enoximone is administered in inhalation form, it is preferable that the effective release of the active substance is situated in a range from 0.01 to 15 mg, preferably from 0.01 to 8 mg preferably at least 0.05 mg, more preferably at least 0.1 mg, even more preferably at least 0.2 mg and most preferably at least 0.3 mg, for example 0.5 mg. Furthermore, the quantity is preferably at most 15 mg, more preferably at most 10 mg, even more preferably at most 8 mg and most preferably at most 5 mg.

The substance can be made available as a suspension, for example in 5, 10, 20, 50 or 100 ml containers. The aroyl-2H-imidazol-2-on, preferably enoximone content can for example be 1 mg/ml.

When aroyl-2H-imidazol-2-on, preferably enoximone is administered in cream form, it is preferable that the effective concentration (w/w) of aroyl-2H-imidazol-2-on, preferably enoximone in the cream is situated in a range from 0.01 to 10%, preferably at least 0.05%, more preferably at least 0.8%, and preferably at most 8%, more preferably at most 5%, even more preferably at most 3%.

Below are examples of some other forms of administration:

Enema:
this would be a fluid/suspension that would be applied anally or rectally (also by the patients themselves) with a maximum effective enoximone dose of 250 mg/day, upon prescription by the treating physician.

Vaginal Tablet:
a semi-solid or solid form of enoximone mixed with a suitable medium; this medium ensures a regulated release. Maximum dose of 250 mg/day, upon prescription by the treating physician.

Suppository:
a semi-solid or solid form of enoximone mixed with a suitable medium; the enoximone is absorbed through resorption. Maximum dose of 250 mg/day, upon prescription by the treating physician.

Transdermal Patches:
a patch that regulates delayed release over a period of time. Maximum dose of 100 mg/day, upon prescription by the treating physician.

Patch:
a patch that is designed for release of enoximone on the skin and that releases enoximone in a maximum dosage of 100 mg/day, preferably at most 75 mg/day.

Injectable depot preparation (subcutaneous or intracutaneous or intramuscular) with delayed release:
comparable to an injectable contraceptive administered once per period (e.g. every three months). In this case, the enoximone is mixed with an oily emulsion that enables the delayed release; maximum dosage of 1000 mg per administration. The administration can be performed via an outpatient centre or the GP.

Sublingual:
A preparation intended for sublingual administration is a preparation that is orodispersible. Orodispersible means that said (preferably solid) preparation will disintegrate in the oral cavity in typically less than 60 s, less than 50 s or less than 40 s without the intake of any liquids. Sublingual is a particular case of orodispersible by which systemic absorption is favoured and first pass metabolisation bypassed. The result is that action can be much faster compared to standard oral dosage forms (as long as the molecule is absorbed through the oral mucosa) and bioavailability can be also higher. Sublingual application is particularly attractive as a rescue treatment for patients that are unable to uptake liquids. In an embodiment, a sublingual preparation is a preparation that releases an aroyl-2H-imidazol-2-on, preferably enoximone or a pharmaceutically acceptable salt thereof in a manner that does not involve an act of inhalation or swallowing by a subject, thus avoiding stress. In this case the active compound can be formulated as described above for a solid preparation, in dosage forms of 5, 10, 15, 20, 25, 50, or 100 mg, upon prescription by the treating physician. Alternately, the active compound can be formulated as a spray or as drops or as another liquid preparation as described above. Preferably, the active compound can be formulated as an orally dissolvable film that provides desired absorption levels of the active compound while providing an adhesive effect in the mouth, rendering it stable at its location.

Gum or Chewing Gum
A preparation intended for the administration of maintenance doses of aroyl-2H-imidazol-2-on, preferably enoximone or a pharmaceutically acceptable salt thereof in a form that a subject would not associate with stressful medical treatment. Maximum dose of 250 mg/day, upon prescription by the treating physician. A gum with a lower dosage of active compound can also be used to prevent symptoms when a subject anticipates the onset of these symptoms. Preferably, a flavouring agent that is released from the gum at a rate similar to aroyl-2H-imidazol-2-on provides an indication of whether the active compound has been fully or sufficiently released from the gum.

Enoximone may also be formulated to be administrated as a soap, cream, shower gel/cream and/or shampoo in dosage forms of 5, 10, 15, 20, 25, 50, or 100 mg per dose.

In an embodiment of the invention, the use of an aroyl-2H-imidazol-2-on, preferably enoximone or a pharmaceutically acceptable salt thereof is its use for the preparation of a medicament for preventing, delaying, ameliorating and/or treating a disease or condition in a subject, wherein said disease or condition is preferably refractory asthma, difficult-to-treat asthma, stable asthma, acute asthma, corticosteroid-resistant asthma, aggravated asthma as a result of an inflammatory reaction, an allergy or any allergic disorder wherein IgE is produced such as hay fever, allergies to domestic animals, constitutional eczema, allergic rhinitis and contact allergies, or COPD. Each feature of this use has been already defined herein.

In an embodiment of the invention, a pharmaceutical composition comprising aroyl-2H-imidazol-2-on, preferably enoximone or a pharmaceutically acceptable salt thereof in an active effective quantity, preferably in a dosage unit of 5, 10 or 20 mg, based on the quantity of the active ingredient, is provided. Such a composition preferably comprises suitable excipients. Such a composition is preferably for use as a medicament for the treatment of atopic and immune-related disorders, preferably by modulating the immune system involved in atopic and immune-related disorders. In said pharmaceutical composition, said aroyl-2H-imidazol-2-on can be enoximone or a pharmaceutically acceptable salt thereof. Each feature of this pharmaceutical composition has been already defined herein.

Said pharmaceutical composition is preferably for use as a medicament for at least one atopic and immune-related disorder chosen from the list of: refractory asthma, difficult-to-treat asthma, stable asthma, acute asthma, corticosteroid-resistant asthma, aggravated asthma as a result of an inflammatory reaction or an allergy or allergic disorder wherein IgE is produced such as hay fever, allergies to domestic animals, constitutional eczema, allergic rhinitis, food allergies and contact allergies, and COPD. Said medicament is preferably for subjects that show limited or no response to treatment with at least one of the following: beta-2 agonists, parasympatholytics, anticholinergics, aminophyllines, magnesium sulphate, corticosteroids and cytostatics.

The dosage and frequency of the above-mentioned forms can be adjusted according to the body weight, the patient's experiences, and findings from future tests and experiments. Initial dosages can be estimated from in vivo data, e.g., animal models, using techniques that are well known in the art. One having ordinary skill in the art could readily optimize administration to humans based on animal data. The amount of molecules administered will, of course, be dependent on the subject being treated, on the subject's weight, the severity of the affliction, the manner of administration and the judgment of the prescribing physician. The moment of administration can be based on the moment of the occurrence of symptoms, for example according to the patient's experiences with regard to the disorder. The moment of administration can be based on a dosage regime that can comprise daily administrations, or less frequent administrations such as once every four days, twice a week, or weekly or each two weeks or each three week or monthly or even less frequently. A relatively less frequent administration (i. e. once every four days, twice a week, or weekly or each two weeks or each three week or monthly or even less frequently) is attractive since possible toxicity or side effect is minimized, costs are minimized and patient's freedom and self image are optimized. In addition such less frequent administration allows a de-escalation regime: the patient himself may decrease the frequency of administration based on his own perceived symptoms.

Aroyl-2H-imidazol-2-on, preferably enoximone can be administered or taken in an appropriate manner in daily, multi-daily, weekly or multi-weekly doses.

The use of Aroyl-2H-imidazol-2-on, preferably enoximone in accordance with this invention in the treatment of asthma, COPD, and other atopic or immune-related disorders such as allergy can be combined in an appropriate manner with the traditional treatment with beta-2 agonists, catecholamines, aminophyllines, corticosteroids, parasympatholytics, magnesium sulphate and combinations thereof. However, Aroyl-2H-imidazol-2-on, preferably enoximone can also be the drug of choice. The treatment of allergic or immune-related disorders with enoximone can additionally be combined with the traditional medication for these disorders, such as anticholinergics and, in severe cases, corticosteroids and cytostatics. Such a combination may be attractive as expected to be synergistic as Aroyl-2H-imidazol-2-on, preferably enoximone on one hand and traditional treatments mentioned above (i.e. beta-2 agonists, catecholamines, aminophyllines, corticosteroids, parasympatholytics, magnesium sulphate, cytostatics) on the other hand work via distinct pathways.

In an embodiment, aroyl-2H-imidazol-2-on, preferably enoximone is for use as defined herein wherein the subjects show limited or no response to treatment with at least one of the following: beta-2 agonists, parasympatholytics, anticholinergics, aminophyllines, magnesium sulphate, corticosteroids and cytostatics. In an embodiment, such subject may be considered to have corticosteroid-resistant asthma.

Experience and research have shown that enoximone is extremely suitable for the above purposes. Intravenous administration in cases of asthma leads to improved breathing within as little as one minute, and within ten minutes if administered orally. As maintenance medication, it ensures lasting (from a few days to several weeks or several months) improvement of the dyspnoea symptoms and the underlying inflammatory and immune-related disorders.

In the case of allergic disorders, the effect may be less immediate; it takes an average of 1 to 3 weeks for any improvement to be noticeable. This is especially the allergic disorder is eczema.

Research has shown that treatment of all of the above forms of asthma is surprisingly adequate, and above all, immediate. It is possible to taper the traditional medication relatively rapidly or even to abandon it altogether. Administration of aroyl-2H-imidazol-2-on, preferably enoximone has also shown to decrease the symptoms and/or parameters of other immune-related atopic disorders, such as asthma.

For asthma as well as COPD and allergic and other atopic or immune-related disorders, the traditional maintenance medication can in most cases partially or even completely be discontinued. Surprisingly efficient and significant immune modulatory results were obtained when aroyl-2H-imidazol-2-on, preferably enoximone was administered at low doses and/or at a low frequency. Low doses in this context means less than 10 mg per day, or 0.01 to 8 mg per day or less. Potential side effects may be circumvented through the use of such low doses. In the context of the invention, low frequency means the present invention allows for dosage regimes that involve an intake schedule featuring intake moments that occur daily, once every four days, weekly, twice a week, preferably six, five, four, or three times a week, more preferably even less often (once per week, once per month, every two, three, four month or even less often), thus relieving the burden on the patient. Upon approval with the physician, the patient may even be allowed to adapt his/her intake schedule depending on the symptoms (i.e. deescalating regime).

Treatment with enoximone and the subsequent decrease of complaints and recovery of condition, will improve the quality of life of many patients considerably. Moreover, due to the low production costs compared to current traditional medication, the costs of treating asthma can be brought down significantly.

In a further aspect there is provided a method for preventing, delaying, ameliorating and/or treating a disease or condition in a subject, wherein said disease or condition is preferably asthma, preferably refractory asthma, difficult-to-treat asthma, stable asthma, acute asthma, corticosteroid-resistant asthma, aggravated asthma as a result of an inflammatory reaction, COPD, allergy, food allergies, allergic reaction or allergic disorders wherein IgE is produced such as hay fever, allergies to domestic animals, constitutional eczema, allergic rhinitis and contact allergies, said method comprising administering to said subject an aroyl-2H-imidazol-2-on, preferably enoximone in any of the formulations described above, or a composition as described above, or a preparation as described above. Optionally, this method can further comprise providing an additional pharmaceutical composition to said subject. Optionally, this method can further be characterised by its dosage regime, which can comprise daily doses, or doses that are administered six, five, four, three, two, or one times per week, or less often. Each feature of this method has been already defined herein.

The invention further provides an in vitro method for inhibiting in a sample a phosphodiesterase activity in cells or the activity or proliferation of peripheral blood mononuclear cells, said method comprising treating said sample with aroyl-2H-imidazol-2-on or a pharmaceutically acceptable salt thereof, preferably in a preparation or formulation or composition as described earlier herein. Each feature of this in vitro method has been already defined herein.

FURTHER ASPECTS OR EMBODIMENTS OF THE INVENTION

These are the original claims in text shape, to not lose any of the text and priority In aspect one, there is provided a use of enoximone or a pharmaceutically acceptable salt thereof for modulation of the immune system involved in atopic and immune-related disorders.

Embodiment one within aspect one provides said use comprising administration of enoximone in oral or topical form, as a suppository or injectable preparation, for example as an injectable depot preparation.

Embodiment two within aspect one provides said use, comprising use of aroyl-2H-imidazol-2-on, in particular (1,3-dihydro-4-methyl-5-[4-(methylthio)benzoyl]-2H-imidazol-2-on) or a pharmaceutically acceptable salt thereof. Embodiment one and two could be combined together.

Embodiment three within aspect one provides said use, comprising administration in oral form of a quantity of active substance situated in a range from 0.01 to 2 mg/kg of body weight, preferably at least 0.05 mg/kg, more preferably at least 0.1 mg/kg, even more preferably at least 0.2 mg/kg and most preferably at least 0.25 mg/kg; and preferably at most 1.5 mg/kg, more preferably at most 1 mg/kg, even more preferably at most 0.8 mg/kg and most preferably at most 0.5 mg/kg. Embodiment three could be combined with embodiment one and/or two.

Embodiment four within aspect one provides said use, comprising administration in inhalation form in a quantity whereby the effective release of active substance is situated in a range from 0.01 to 15 mg, preferably at least 0.05 mg, more preferably at least 0.1 mg, even more preferably at least 0.2 mg and most preferably at least 0.3 mg, for example 0.5 mg; and preferably at most 15 mg, more preferably at most 10 mg, even more preferably at most 8 mg and most preferably at most 5 mg. Embodiment four could be combined with embodiment one and/or two and/or three.

Embodiment five within aspect one provides said use, for treatment of at least one atopic and immune-related disorders, for example refractory asthma, difficult-to-treat asthma, stable asthma, acute asthma, aggravated asthma as a result of an inflammatory reaction or an allergic reaction, and COPD, with limited or no response to treatment with at least one of the following: beta-2 agonists, parasympatholytics, anticholinergics, aminophyllines, magnesium sulphate, corticosteroids and cytostatics. Embodiment five could be combined with embodiment one and/or two and/or three and/or four.

Embodiment six within aspect one provides said use, in solid form, as dispersible tablet, effervescent tablet, coated tablet, tablet with delayed release, capsule or powder, with an optionally added adjuvant or carrier. Embodiment six could be combined with embodiment one and/or two and/or three and/or four and/or five.

Embodiment seven within aspect one provides said use in fluid form, wherein enoximone is added to a compatible dissolving, suspending or emulsifying medium. Embodiment seven could be combined with embodiment one and/or two and/or three and/or four and/or five.

Embodiment eight within aspect one provides said use in cream form, wherein enoximone is added to a compatible dermatological medium. Embodiment eight could be combined with embodiment one and/or two and/or three and/or four and/or five.

Embodiment nine within aspect one provides said use as an enema, comprising a fluid suspension of enoximone in a maximum effective dose of 250 mg/day. Embodiment nine could be combined with embodiment one and/or two and/or three and/or four and/or five.

Embodiment ten within aspect one provides said use as a vaginal tablet in a semi-solid form, comprising enoximone mixed with a suitable medium in a maximum effective dose of 250 mg/day. Embodiment ten could be combined with embodiment one and/or two and/or three and/or four and/or five.

Embodiment eleven within aspect one provides said use as a suppository in a semi-solid form, comprising enoximone mixed with a suitable medium in a maximum effective dose of 250 mg/day, wherein the enoximone can be absorbed in the body through resorption. Embodiment eleven could be combined with embodiment one and/or two and/or three and/or four and/or five.

Embodiment twelve within aspect one provides said use as a transdermal patch, in a maximum effective dose of 100 mg/day, preferably as a patch with delayed release.

Embodiment twelve could be combined with embodiment one and/or two and/or three and/or four and/or five.

Embodiment thirteen within aspect one provides said use as an injectable preparation, subcutaneous or intramuscular, preferably as a depot preparation with delayed release wherein the enoximone preparation is mixed with an oily emulsion, in a maximal dose of 1000 mg per administration. Embodiment thirteen could be combined with embodiment one and/or two and/or three and/or four and/or five.

In aspect two, there is provided a pharmaceutical composition comprising aroyl-2H-imidazol-2-on or a pharmaceutically acceptable salt thereof in an active quantity in the treatment of atopic and immune-related disorders, especially for modulating the immune system involved in atopic and immune-related disorders. Guido Embodiment one within aspect two provides a pharmaceutical composition in a dosage unit of 5, 10 or 20 mg, based on the quantity of the active ingredient.

In aspect three, there is provided a pharmaceutical preparation in cream form, comprising enoximone in a pharmaceutically active concentration, preferably in a range from 0.01 to 10%, preferably at least 0.05%, more preferably at least 0.8% and preferably at most 8%, more preferably at most 5%, even more preferably at most 3% (w/w), based on the weight of the composition.

In aspect four, there is provided a pharmaceutical preparation in fluid form as a suspension or solution for use as an enema, comprising enoximone in a maximum effective dose of 250 mg/day, preferably at most 200 mg/day.

In aspect five, there is provided a pharmaceutical preparation in semi-solid form for use as a suppository, formed from a composition of enoximone in a suitable medium, comprising enoximone in a maximum dosage of 250 mg/day, preferably at most 200 mg/day, preferably configured for delayed release of enoximone in the body through resorption.

In aspect six, there is provided a pharmaceutical preparation in semi-solid form for use as a vaginal tablet, formed from a composition of enoximone in a suitable medium, comprising enoximone in a maximum dosage of 250 mg/day, preferably at most 200 mg/day, preferably configured for delayed release of enoximone.

In aspect seven, there is provided a pharmaceutical preparation in the form of a transdermal patch comprising enoximone, configured for delayed release of enoximone in a maximum dosage of 100 mg/day, preferably at most 75 mg/day.

In aspect eight, there is provided a pharmaceutical preparation in the form of a patch comprising enoximone, configured for delayed release of enoximone on the skin in a maximum dosage of 100 mg/day, preferably at most 75 mg/day.

In aspect nine, there is provided a pharmaceutical preparation in the form of an injectable depot preparation for subcutaneous or intracutaneous or intramuscular injection, comprising enoximone in a maximum quantity of 1000 mg and a carrier for delayed release of the active substance, wherein the carrier is preferably formed from an oily emulsion.

Definitions

In this document and in its claims, the verb "to treat" and its conjugations is used preferably to refer to delaying, ameliorating treating, stabilizing or curing a disease or condition, or the progress of a disease or condition, in a subject. Alternatively, a disease or condition can be prevented by treatment.

In this document and in its claims, the verb "to modulate" is used preferably to refer to effecting a change through regulation, adjustment, or adaptation. For example, modulation of the immune system is seen in this document and in its claims as a regulation, adjustment, or adaptation of the immune system, which can be effected through an influence on the activity or proliferation of immune cells or through an influence on the expression or activity of enzymes related to the immune system.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product, an assay device respectively a method or a use as defined herein may comprise additional component(s) respectively additional step(s) than the ones specifically identified, said additional component(s), respectively step(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

EXAMPLES

The invention is explained in more detail below with a number of tests and examples, which are not to be construed as limiting the scope of the invention.

Example 1

Trial 1:

A 52 year-old female patient was to be operated in connection with a mammary carcinoma. She had known difficult-to-treat asthma and before the operation she received 30 mg prednisone per day as extra medication in addition to her beta-2 agonists and parasympatholytics treatment, but her breathing remained considerably obstructed. Ten minutes before the start of the anaesthesia she was given 25 mg enoximone intravenously. The asthma symptoms disappeared within a few minutes and the operation could go on as scheduled. During a check-up two weeks after the operation, the patient surprisingly proved still free of asthma symptoms. Ultimately, after a single administration of enoximone, she stayed symptom-free for two months.

Example 2

Trial 2:

Based on the above experience, a second patient was treated. According to her lung specialist, she suffered from untreatable asthma and had been completely bed-ridden for a long time, among other reasons due to high doses of the traditional medication (next to some other drugs she received 50 mg prednisone per day). Inhalation therapy worked for a few minutes only due to the severe bronchoconstriction, the drying of the airways and the consequential sticky obstructive mucus. The patient received 20 mg enoximone orally in two doses of 10 mg at a 15 minutes interval. The asthma symptoms already disappeared within two minutes of the first dose. She remained symptom-free for 7 days. During the first day after the first administration, the patient coughed a lot, which loosened the sticky mucus. After 7 days, she received another 10 mg dose of enoximone orally, after which she again remained symptom-free for 7 days. She was ultimately able to drastically reduce her prednisone use to 5 mg per day (complete phasing out was not possible in connection with her Mixed Connected Tissue Disease). She was able to build up her condition relatively quickly with a maintenance dose of 10 mg of enoximone once every 4 days. After 3 months, she was able to perform her normal household activities again and go back to work. After another month, she was even able to do some sport with caution.

Example 3

Trial 3:

Following trials 1 and 2, several patients with light to severe asthma symptoms, who up to that time had been treated exclusively with the traditional therapy with little or no results, were also treated with enoximone.

They all showed remarkable and fast progress. Their individual dosage depended on the severity of the disorder. The dosage ranged from 0.1 to 0.3 mg/kg body weight, mostly in a maintenance dosage of twice a week, based on the time of recurrence of the symptoms.

Five patients indicated that during treatment with enoximone (among other medication), their allergic and immune-related symptoms also became substantially milder or even disappeared altogether. The combination of effects on both the asthma-related and other symptoms shows that the action of the drug exceeds its physical half-life.

The demonstrated positive effect of enoximone therefore offers a surprising solution to the treatment of asthma in all the above forms, for COPD and other atopic and immune-related disorders. All the patients treated reacted within a few minutes and remained days or weeks symptom-free after only one dose.

A few cases of side effects were noted: two patients reported headaches on the day of intake, which disappeared again after one day. Adjusting (lowering) the dose offered a solution. The comparison with side effects of traditional treatment methods (see above), is largely favourable for enoximone.

Example 4

We surprisingly observed that PDE3 inhibition with enoximone abrogates eosinophilic airway inflammation in an in vivo house dust mite driven mouse model for allergy. Human peripheral blood mononuclear cells (PBMCs) in vitro stimulated with tetanus toxoid showed a diminished T-cell proliferation when treated with enoximone. Human basophils showed reduced activation when treated with enoximone Methods House Dust Mite (HDM) Allergic Airway Inflammation Model To induce airway inflammation, mice were anaesthetized with isofluorane and treated intratracheally (i.t.) with 1-10 µg house dust mite (HDM; Greer Laboratories) allergen extract in 80 µL phosphate buffered saline (PBS) on day 0 or using PBS only. Ten days later, anesthetized mice were challenged with 1-10 µg HDM in 50 µL PBS intranasally (i.n.) for 5 consecutive days. Mice were sacrificed 24 hr after last challenge and broncho alveolar lavage was performed by flushing the lungs 3 times with 1 ml PBS containing Ethylenediaminetetraacetic acid (EDTA, Sigma-Aldrich).

Treatment Strategy 1: HDM Allergy Induction Models

Different treatment modalities were testes i.e. route and dose. Here we tested the oral versus intratracheal route (FIG. 1) and PBS versus enoximone in a HDM driven allergy model. Enoximone was precipitated from Perfan®. The precipitant was admitted with HDM solution and used as a suspension for intratracheal treatment doses 25 µg and 250 µg or it was used as a suspension admitted in PBS for oral treatment doses 250 µg or 2.5 mg. Mice underwent enoximone treatment only during challenge. Sensitization was performed with 1 µg HDM and challenge with 2.5-5 µg HDM. Twenty-four hours after the last challenge measurements were performed.

Optimal dose of 25 µg enoximone versus diluent (FIG. 5) was admitted with 5 µg HDM solution and used for intratracheal treatment or diluent (10% ethanol+40% glycerol+50% MQ) admitted with 5 µg HDM solution. Controls were treated with enoximone 25 µg admitted with PBS or diluent admitted with PBS. Mice underwent enoximone treatment only during challenge.

Treatment Strategy 2: Established HDM Allergy Model

C57bl/6 mice were sensitized with 10 µg HDM on day 0 and challenged with 5 µg HDM for 5 days on day 10-14. Then mice were treated with 5 µg HDM admixed with 25 µg enoximone or diluent for 5 days on days 15-19. 24 hr after last challenge measurements were performed.

Human PBMC Proliferation Assay

PBMCs obtained from buffy coats were isolated by using Ficoll-Paque (density 1.077 g/cm$^3$) density gradient centrifugation. After washing, cells were frozen via a cool down procedure by admixing with dimethyl sulfoxide (DMSO, final concentration 10%) and gradually cooled till minus 80° C. and stored in minus 180° C. until use. Stored PBMCs were thawed and washed 2 times with RPMI containing 10% heat-inactivated fetal bovine serum, gentamycine and β-mercaptoethanol, labelled with Carboxyfluorescein succinimidyl ester (CFSE) and seeded at 2×10$^5$ cells/well in 96 round bottom wells plates in the presence of tetanus toxoid (3Lf/ml, RIVM, Bilthoven, The Netherlands). Cells were cultured in the presence of diluent or enoximone 25 µg/ml. Cells were harvested and quantified by Fluorescence-activated cell sorting (FACS) (CD3, CD4 and CD14 and CD19) after 7-13 days. Proportions of divided and undivided CD4 cells were quantified.

Immunohistochemical Staining

Stainings were performed in a half-automatic stainer (Sequenza). Acetone-fixed slides were washed with PBS and incubated and blocked in diluted normal goat serum (CLB, Amsterdam, the Netherlands). Sections were stained with mouse anti human PDE3A (clone 2D7 Abnova), mouse anti human PDE3B (clone F-9 Santa Cruz Biotechnology) or rabbit anti human PDE4 (Fabgennix). The primary antibody was detected using goat anti mouse long-chain biotinstreptavidin conjugated-alkaline phosphatase (BioGenix) or with goat anti rabbit conjugated-alkaline phosphatase (Sigma). After rinsing, slides were incubated with New Fuchsin substrate. Finally, the sections were counterstained with Gills triple strength haematoxylin and mounted in Vecta Mount (Vector).

Basophil Degranulation Assay

PBMCs including basophils were treated with diluent or several doses of enoximone at 37° C. for half an hour. Next the cells were washed and incubated with anti IgE antibodies 5□g/ml for 20 minutes at 37° C. for 20 minutes washed again at 4° C. and consequently stained for flowcytometric with CD123-BV650, CD203c-PE, CD107a-FITC, HLA-DR-PerCPCy5.5 and FcεRI-APC at 4° C. for 30 minutes. Cells were acquire with a LSRII and analyzed with Flowjo X. Basophils were identified as FcεRI+, CD123+ and HLA-DR− cells. Degranulated and/or activated basophils stained positive for CD203c and CD107a. 100% degranulated basophils were set as the % of degranulated basophils treated with diluent and stimulated with 5□g/ml anti IgE. Proportion of inhibition was calculated as % of degranulated basophils divided by the maximal % of diluent treated degranulated basophils.

Statistical Analysis

Reported values are shown as mean±SEM. Statistical analyses were performed with SPSS (SPSS Inc., Chicago, Ill.) using a Mann-Whitney U-test. Resulting p values less than 0.05 (*) and 0.01 (**) are indicated and considered significant. Tests that did not reach significance (p>0.05) are not indicated.

Results:

Immunohistochemistry

The cryostat sections of the lung mucosa and nasal mucosa were stained for PDE3A and PDE3B and PDE4. Staining with monoclonal antibodies for PDE3A and PDE3B could be identified by the PDE3-specific red stain. Staining with polyclonal rabbit and PDE4 antibodies could be identified by the PDE4 specific red stain. A dark violet nucleus-specific staining was performed to characterize the cells (FIG. 1).

We investigated eosinophilic airway inflammation in female C57bl/6 mice subjected to HDM driven model for allergy (part A of FIG. 5). HDM/PBS treated mice demonstrated a clear eosinophilic airway inflammation which was significantly higher in eosinophil numbers when compared to orally (2.5 and 0.25 µg) or intratracheally (25 and 250 µg) enoximone treated mice (part B of FIG. 5). Next we investigated a recently discovered IL-5 and IL-13 producing innate lymphocyte (ILC2) which shows the same dynamic and is reduced upon enoximone treatment (part C of FIG. 5). Neutrophils, T-cells, and DCs show a similar pattern and were significantly higher in the PBS treated allergy mice. Control mice treated with PBS diluent or PBS/enoximone showed no eosinophilic airway inflammation.

Next, we investigated if enoximone solution admitted to the HDM solution is effective when given intratracheally (part A of FIG. 6.). HDM 5 µg in 45 µl PBS and 5 µl diluent (10% ethanol+40% glycerol+50% MQ) treated mice demonstrated significantly higher numbers of BAL eosinophils compared to enoximone treated mice (FIG. 6B). Next we investigated neutrophils and ILC2 cell numbers and in line with the eosinophil pattern, the same dynamic is observed for neutrophils and ILC2s indicating the efficacy of enoximone in this HDM-driven asthma model (parts C and D of FIG. 6). Control mice treated with PBS diluent or PBS/enoximone showed no signs of allergic airway inflammation.

Enoximone Treatment Reduces Eosinophilic Inflammation During Ongoing Inflammation Next, we attempted to determine whether enoximone is potent enough to suppress allergic inflammation when asthma is already fully established. Animals were challenged with an additional session of 5 challenges with HDM mimicking the situation in asthma patients. Asthma mice and PBS controls were then challenged again on five successive days by instilling a droplet of 50 µl PBS (PBS PBS dil), or HDM (5 µg) in 50 µl PBS (HDM HDM dil) or HDM (5 µg) in 50 µl PBS admixed with enoximone (25 µg) (HDM HDM enox)(FIG. 7A). When enoximone treatments were started after the first 5 HDM challenges, the enoximone-treated mice showed strong significant reductions in eosinophil numbers indicating that enoximone treatment was able to speed up the recovery (part B of FIG. 7).

In line with these data, numbers of ILC2s, T-cells and macrophages also showed significant reduction in numbers when animals were treated with enoximone (parts C, D and E of FIG. 7). Enoximone abrogates established allergic airway inflammation in a mouse HDM model.

Lower Enoximone Treatment Frequency is Effective as Daily Enoximone Treatment Frequency in Reducing Eosinophilic Airway Inflammation.

Next we investigate if it is possible to lower the active enoximone treatment frequency when given it admixed to the HDM challenge solution (FIG. 2A). We compare the daily treatment frequency with once in two days (each other day) and once in three days. Mice treated with HDM admixed with diluent show clear eosinophilic airway inflammation (FIG. 2B). When mice treated with HDM admixed with enoximone a clear reduction in eosinophilic inflammation could observed when enoximone was given every day, once in two days (each other day) and once in three days (FIG. 2B). Moreover along this line also numbers of T-cells drop when treated with enoximone (FIG. 2B). Next we investigate the number of T-cells producing cytokines important in allergic airway inflammation and here we observed that all investigated cytokines (IL-4, IL-5, IL-13, IL-17 and IFNγ) producing T-cells important in allergic inflammation drop in number (FIG. 3). Moreover the proportion of IL-4 producing T-cells is lower when enoximone is given less frequently than daily (FIG. 3).

Human PBMC proliferation, induced by the stimulation with tetanus toxoid, was reduced for CD4 positive T-cells when they were cultured in the presence of enoximone. This indicates a direct effect of enoximone on tetanus toxoid-induced T-cell proliferation and can be considered an anti-inflammatory effect.

Human Basophil Activation is Reduced when Treated with Enoximone

Human PBMCs contains basophils. Basophils could be activated and stimulated by anti IgE with the consequence of crosslinking FcεRI. Crosslinking of FcεRI induce the activation and degranulation of basophils with the consequence of an upregulation of CD63, CD107a and CD203c. Here we observed that if basophils were treated with enoximone (20-1000 µM) a reduced basophil activation (CD107a and CD203c positivity) was seen when stimulated with anti IgE. A more than 50% inhibition was already seen at a concentration of 20 µM enoximone which increase till above 90% at a concentration of 1000 µM (FIG. 4).

Conclusion

PDE3 and PDE4 are detectable in human airway mucosa, in bronchial mucosa, as well as in nasal mucosa. PDE3 inhibition by enoximone reduces eosinophilic airway inflammation in a house dust mite (HDM) allergy model as measured in the bronchoalveolar lavage (BAL). This reduction could observed when treatment was given orally, which can be marked as a systemic therapy, or when treatment was given topically by admixing enoximone with HDM solution followed by intratracheal administration, which can be marked as a topical therapy. Human immune cells are sensitive for enoximone. Human basophils showed reduced activation when treated with enoximone and CD4 T-cell proliferation is diminished when treated with enoximone.

Below we provide several non-limiting examples of enoximone formulations (tablets or aqueous suspension for inhalation). In each of the examples below, each of the specific substances used in combination with enoximone may have been replaced by another equivalent substance having the same function as indicated in the table (i.e other filler, binder, disintegrant, lubricant, glidant, sweetener, flavor, viscosity modifier, surfactant, tonicity agent, complexing agent, preservative and/or carrier).

Immediate Release (IR) tablets or capsules: the active drug substance can be in crystalline or amorphous form.

Example 5

Direct Compression IR Tablet

Direct compression formulations are prepared by dry blending of components.

| Component | mg | Action |
|---|---|---|
| Enoximone | 10 | Active drug substance |
| Lactose | 50 | |
| Microcrystalline cellulose | 30 | Filler |
| | 4.5 | Filler/binder |
| Croscarmellose sodium | 0.5 | Disintegrant |
| Magnesium stearate | | Lubricant |
| Total | 100 | |

Example 6

Direct Compression IR Tablet

| Component | mg | Action |
|---|---|---|
| Enoximone | 10 | Active drug substance |
| Lactose | 75 | |
| Povidone | 10 | Filler |
| Crospovidone | 4.5 | Binder |
| Magnesium stearate | 0.5 | Disintegrant Lubricant |
| Total | 100 | |

Example 7

Wet Granulation IR Tablet

Wet granulation involves mixing of excipients and drug substance with a binder solution using granulation equipment. Addition of extra-granular excipients is also part of the process; the formula below shows the overall composition without differentiating intra and extragranular components.

| Component | mg | Action |
|---|---|---|
| Enoximone | 10 | Active drug substance |
| Microcrystalline cellulose | 158 | |
| | 10 | Filler |
| Povidone | 21 | Binder |
| Sodium starch glycolate | 1 | Disintegrant |
| Magnesium stearate | | Lubricant |
| Total | 200 | |

Example 8

Capsule Composition

Granules manufactured as above and filled into capsules (e.g. hard gelatin).

| Component | mg | Action |
|---|---|---|
| Enoximone | 20 | Active drug substance |
| Microcrystalline cellulose | 108 | |
| | 6 | Filler |
| Povidone | 15 | Binder |
| Croscarmellose sodium | 1 | Disintegrant |
| Hydrophobic silica | | Glidant |
| Total | 150 | |

Orodispersible tablets (ODT): the active drug substance can be in crystalline or amorphous form. Manufactured as direct compression.

Example 9

| Component | mg | Action |
|---|---|---|
| Enoximone | 10 | Active drug substance |
| Mannitol | 82.6 | |
| Crospovidone | 5 | Filler |
| Acesulfame K | 0.5 | Binder |
| Hydrophobic silica | 0.5 | Sweetener |
| Magnesium stearate | 1 | Glidant |
| Orange flavour | 0.3 | Lubricant |
| Peppermint flavour | 0.1 | Flavour Flavour |
| Total | 100 | |

Aqueous suspension for nasal inhalation: the active drug substance is micronised.

Example 10

Aqueous Suspension Buffered at pH 4.5

| Component | % (w/w) | Action |
|---|---|---|
| Enoximone | 0.06 | Active drug substance |
| Croscarmellose sodium | 0.15 | |
| Polysorbate 80 | 0.05 | Viscosity modifier |
| Sodium chloride | 0.9 | Surfactant |
| Disodium edetate | 0.05 | Tonicity agent |
| Benzalkonium chloride | 0.02 | Complexing agent |
| Water for injection | q.s. | Preservative Carrier |

It can be concluded based on the tests described above that treatment with enoximone, possibly in addition to the traditional treatment, is a very adequate and advantageous approach for patients with asthma, allergy, COPD and other atopic and immune-related disorders. Traditional medication, with often harmful side effects, can often be tapered down or sometimes even discontinued. Other expensive treatments can possibly be omitted. In addition to the fact that the patients' quality of life can be improved considerably thanks to treatment with enoximone, this treatment offers substantial cost savings to society.

The invention is not limited to the forms of implementation described above in the trials given as examples. The invention is only limited by the attached conclusions.

The invention also extends to each combination of measures as described above, independently from each other.

(A) Experimental HDM asthma design showing intratracheal sensitisation (s) of 10 µg HDM or PBS as control and challenge (c) with 10 µg HDM intra nasal. The following schedules were used diluent (d) (5 µl) during challenge (for 5 days ddddd), enoximone (5 µl 5 mg/ml) during challenge (for 5 days eeeee), enoximone once in two days (edede) or (deded) and once in three days enoximone (edded). (B) Total cells and quantification of flow cytometric analyses of eosinophils and CD4 T-cells in BAL of PBS treated (black bars) and several frequencies of enoximone treated mice (gray bars). Results are expressed as means±SEM.

Figure 1:
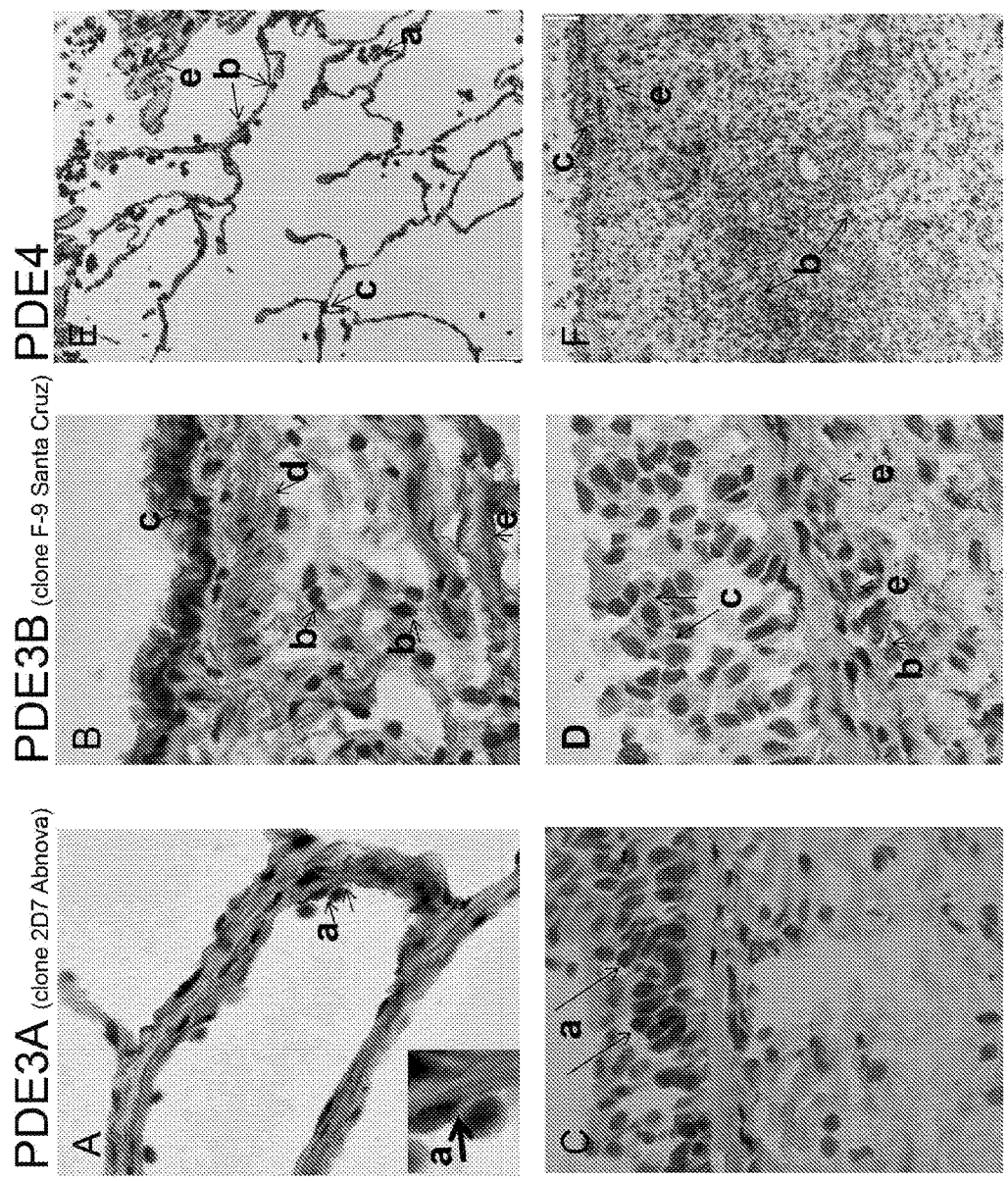
FIG. 1 Human lung mucosal sections of (A) lung parenchyma (alveolar tissue) and (B) Bronchus mucosal tissue. Clear expression of PDE3A protein in grey and arrows is observed in (a) endothelial cells in a vessel along alveoli and PDE3B protein is observed pointed by arrows in the bronchus mucous in inflammatory cells (b) and structural cells like: epithelium (c), muscle cells (d) and endothelium cells (e). Human nasal mucosal sections of inferior turbinates stained (grey and arrows) for PDE3A (C) and for PDE3B (D). Epithelial cells (a) stained positive for PDE3A. Endothelial cells (e), epithelial cells (c) and inflammatory cells (b) stained positive for PDE3B. Human lung mucosal tissue (E) and nasal mucosal tissue (F) stained positive for PDE4 pointed by arrows. Alveolar macrophages (a) endothelial cells (e) pneumocytes (c) and inflammatory cells (b) stained positive for PDE4 in lung mucosa. Inflammatory cells (b) epithelial cells (c) and endothelial cells (e) stained positive for PDE4 in the nasal mucosa (F).
Figure 2:
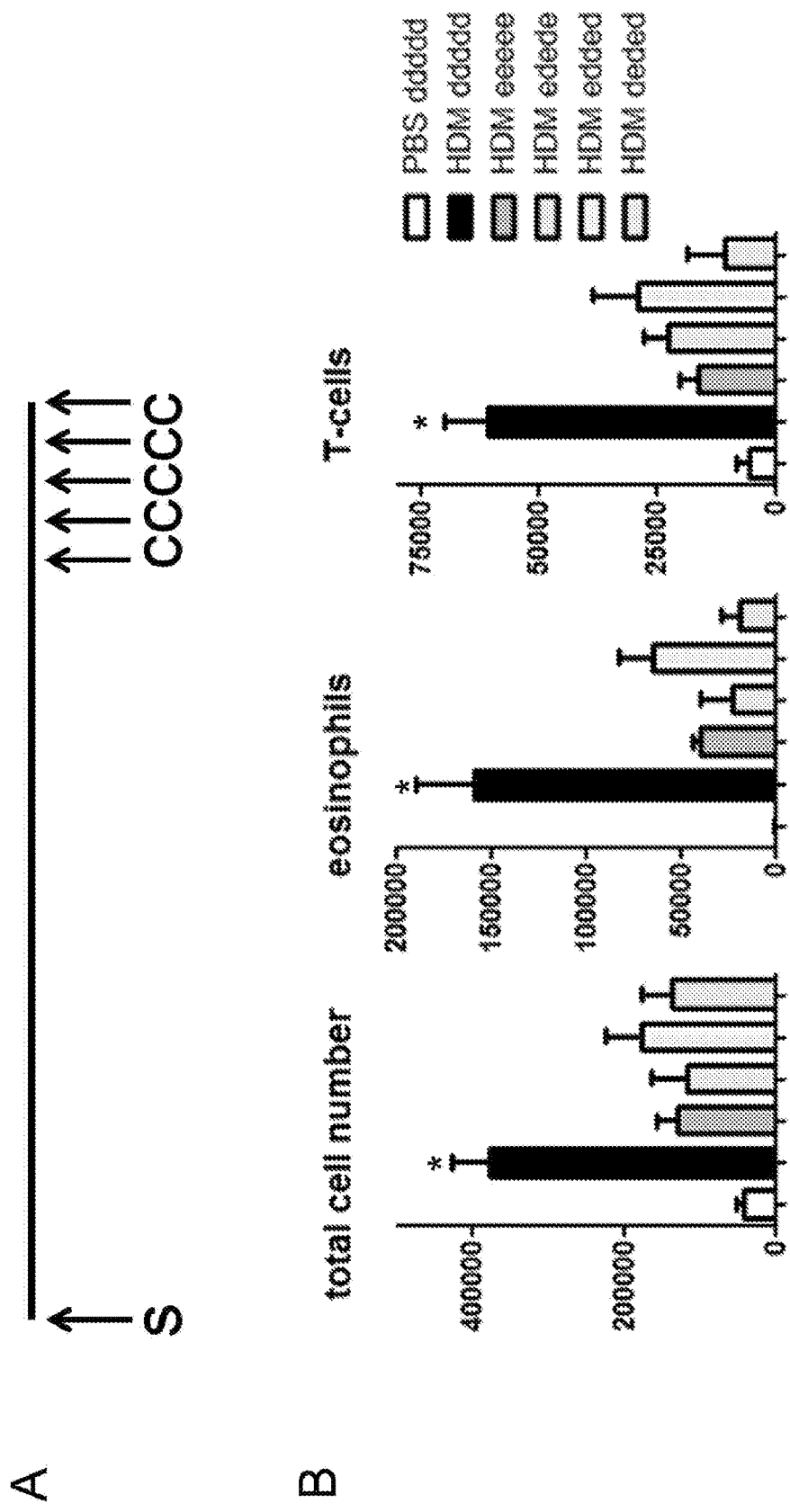
FIG. 2 Topical daily or once per 2 days or once per 3 days (intratracheal) treatment with 25 µg enoximone reduced allergic airway inflammation in a house dust mite asthma model.
Figure 3:
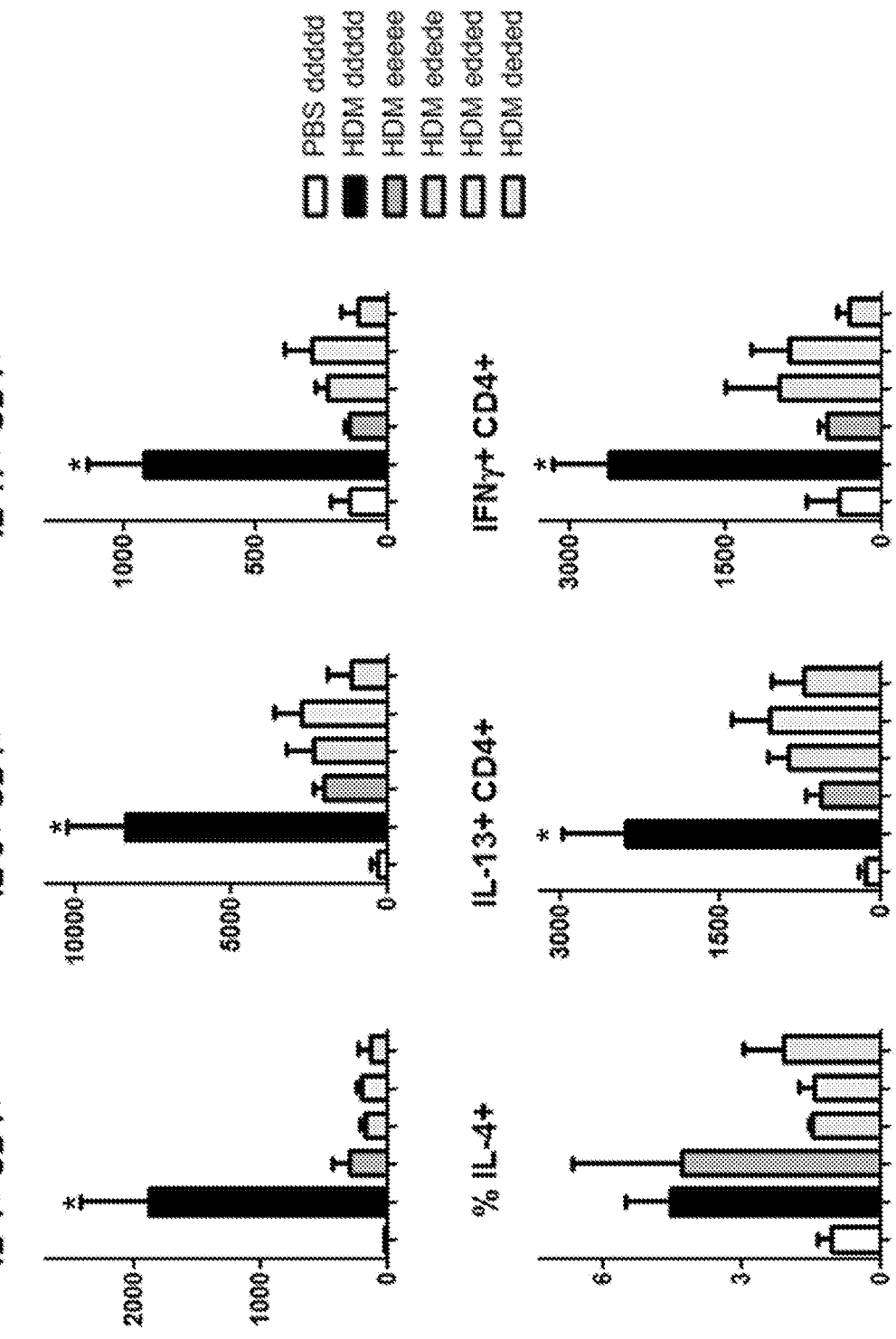

FIG. 3 Quantification of flow cytometric analyses of cytokine producing CD4 T-cells and proportion of IL-4 positive CD4 T-cells in BAL. Results are expressed as means±SEM. n=3-8 animals per group. Statistical evaluations were performed only between different treatments of groups (*p<0.05).

Figure 4:
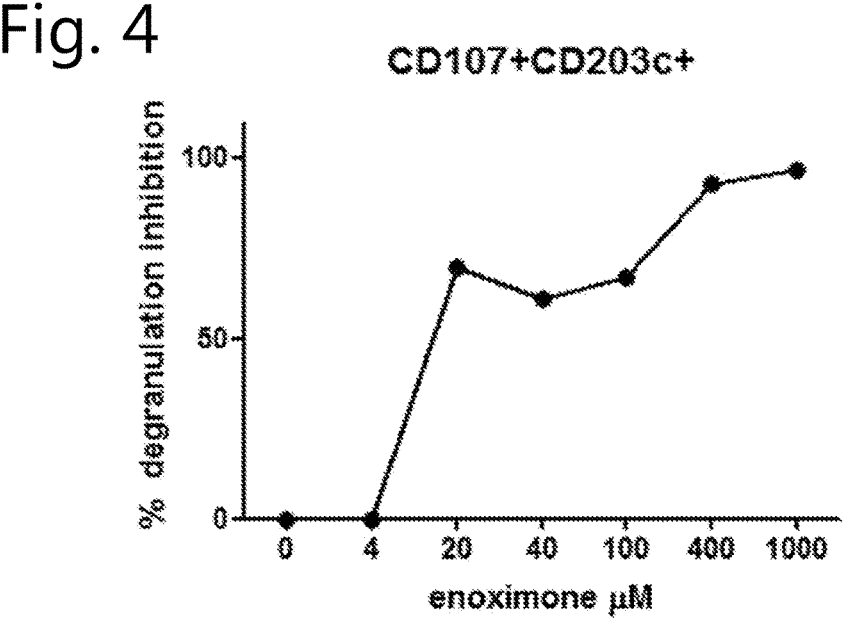

FIG. 4 Human PBMCs including basophils were treated with diluent or several doses of enoximone and cells were activated by incubation with anti IgE antibodies. Data plotted show the mean proportion of inhibition was calculated as % degranulated basophils (CD123$^+$FceRI$^+$HLA-DR$^-$CD107a$^+$CD203c$^+$ cells) pretreated with enoximone divided by % of diluent treated degranulated basophils (n=3).

Figure 5:
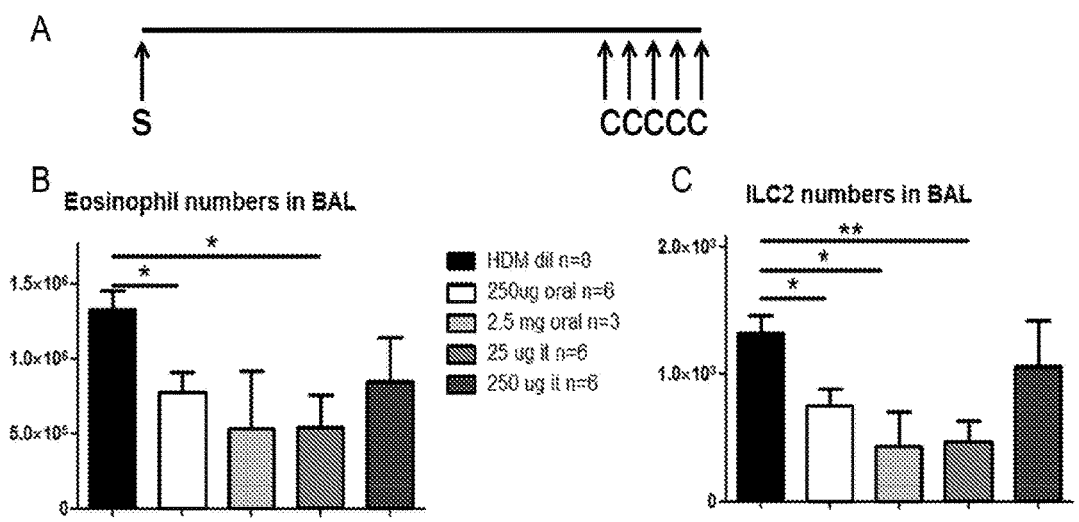

FIG. 5 Systemic (Oral) and topical (intratracheal) treatment with enoximone reduced allergic airway inflammation in a house dust mite asthma model.

(A) Experimental HDM asthma design showing intratracheal sensitisation (s) of 1 µg HDM or PBS as control and five intra-nasal challenges (c) with 2.5-5 µg HDM. (B) Quantification of flow cytometric analyses of the indicated populations of eosinophils in bronchoalveolar lavage (BAL) of PBS treated mice (black bars) and enoximone treated mice (white and greyscale bars). Results are expressed as means±SEM. (C) Quantification of flow cytometric analyses of ILC2 numbers in BAL. Results are expressed as means±SEM. Results represent data of one out of 2 experiments with 3-8 animals per group. Statistical evaluations were performed only between different treatments of groups. *p<0.05, **p<0.01).

Figure 6:
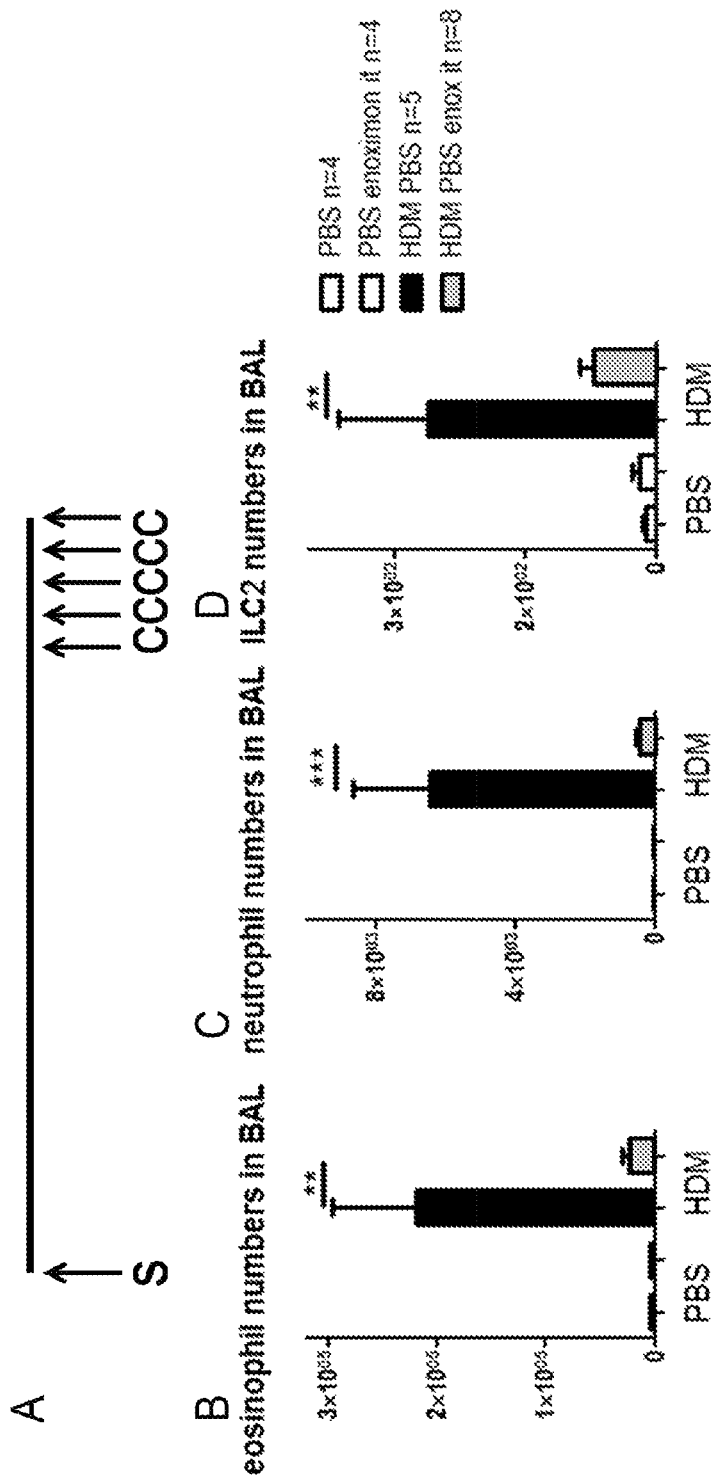

FIG. 6 Topical (intratracheal) treatment with 25 µg enoximone reduced allergic airway inflammation in a house dust mite asthma model.

(A) Experimental HDM asthma design showing intratracheal sensitization (s) of 1 µg HDM or PBS as control and intra nasal challenge (c) with 5 µg HDM. (B) Quantification of flow cytometric analyses of eosinophils in BAL of PBS treated mice (black bars) and enoximone treated mice (light grey bars). Results are expressed as means±SEM. (C) Quantification of flow cytometric analyses of neutrophils and (D) ILC2s in BAL. Results are expressed as means±SEM. n=4-8 animals per group. Statistical evaluations were performed only between different treatments of groups (*p<0.05 or **p<0.01).

Figure 7:
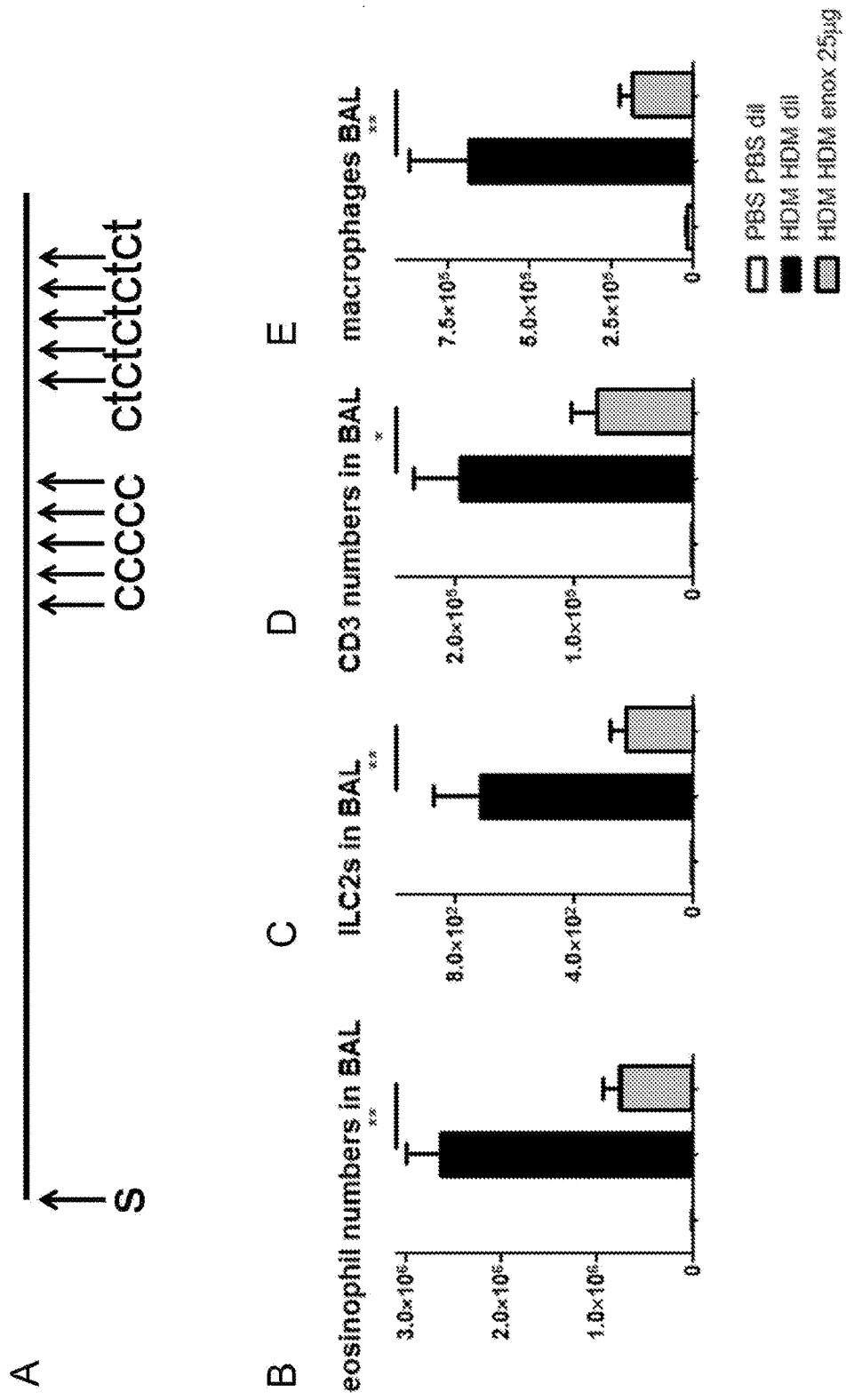

FIG. 7 Topical (intratracheal) treatment with 25 enoximone reduced allergic airway inflammation in established asthma house dust mite asthma model.

(A) Experimental HDM asthma design showing intratracheal sensitization (s) of 1 HDM or PBS as control and intra nasal challenge (c) with 5 µg HDM followed by challenge and treatment (ct). (B) Quantification of flow cytometric analyses of eosinophils in BAL of PBS treated mice (black bars) and enoximone treated mice (light grey bars). Results are expressed as means±SEM. (C) Quantification of flow cytometric analyses of ILC2s, (D) CD3 and (E) macrophages in BAL. Results are expressed as means±SEM. n=4-8 animals per group. Statistical evaluations were performed only between different treatments of groups. (*p<0.05 or **p<0.01).

Figure 8:
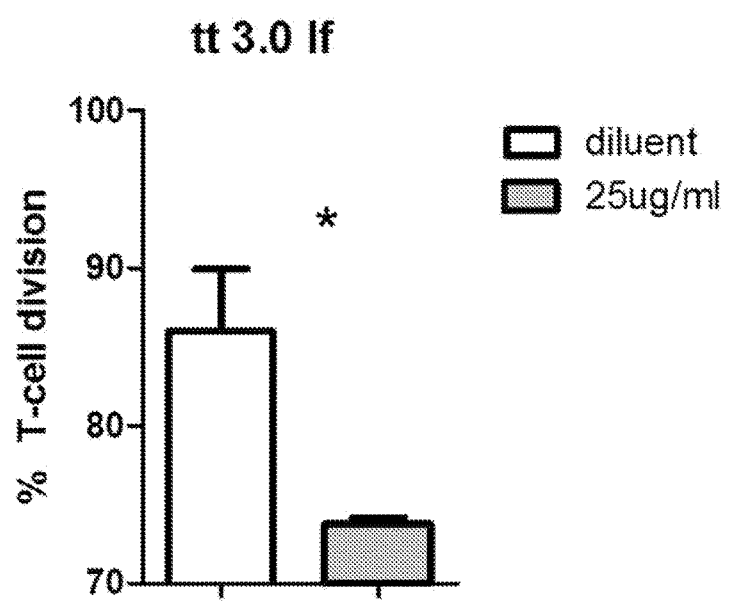

FIG. 8 Human PBMCs were CF SE labeled and stimulated with tetanus toxoid for 7-14 days.

Proportion of divided CD4 T-cells were significantly reduced when cells were cultured in the presence of enoximone 25 µg/ml green bar compared to diluent white bars, indicating an inhibitory effect of enoximone on T-cell proliferation.

The invention claimed is:

1. A method for delaying, ameliorating and/or treating an atopic and immune-related disorder in a subject, wherein said disorder is selected from the group consisting of asthma, refractory asthma, difficult-to-treat asthma, stable asthma, acute asthma, corticosteroid-resistant asthma, aggravated asthma as a result of an inflammatory reaction, COPD, an allergic reaction, and any allergic disorder wherein IgE is produced, said method comprising administering to the subject a dose from .05 mg/kg to 0.5 mg/kg of an aroyl-2H-imidazol-2-on or a pharmaceutically acceptable salt thereof or a pharmaceutical composition comprising a dose from .05 mg/kg to 0.5 mg/kg of an aroyl-2H-imidazol-2-on or a pharmaceutically acceptable salt thereof, wherein said dose is administered no more often than six to two times per week.

2. A method according to claim 1, wherein said disorder is asthma.

3. A method according to claim 1, wherein said disorder is allergy.

4. A method according to claim 3, wherein an improvement of a parameter or a symptom associated with said disorder has a duration of at least 4 hours, or at least 1 day after such compound has been administrated or after the single dose of such compound has been administrated or after the first dose of such compound has been administrated, wherein said symptom associated with said disorder is selected from the group consisting of
  (i) itching, red skin, and urticarial for (domestic) animal allergy, and
  (ii) sneezing, nasal blockage, nasal discharge, itching of the nose, itching of the eye, and itching of the palate, for allergic rhinitis, and
  (iii) difficulty of breathing, wheezing, dyspnea, coughing, chest tightness, sputum production, and nighttime awakenings for asthma, and
  wherein said parameter associated with said disorder is selected from the group consisting of an inhibition of activity of cells of the immune system or a detectable decrease of activity of cells of the immune system, and/or an inhibition of activity or proliferation of T-cells stimulated with an antigen or an allergen or a detectable decrease of activity or of proliferation of such T-cells, and/or an inhibition of activity or proliferation of eosinophils or a detectable decrease of activity or of proliferation of eosinophils, and/or an inhibition of activity or proliferation of ILC2 cells or a detectable decrease of activity or of proliferation of ILC2 cells, and/or an inhibition of activity or proliferation of dendritic cells or a detectable decrease of activity or of proliferation of dendritic cells and/or an inhibition of activity or proliferation of B cells or a detectable decrease of activity or of proliferation of B cells and/or an inhibition of activity or proliferation of macrophages or a detectable decrease of activity or of proliferation of macrophages, and/or a decrease or reduction of the level of IgE.

5. A method according to claim 4, wherein an improvement of said parameter or a symptom associated with said disorder has a duration of or at least 1 day after such compound has been administrated or after the single dose of such compound has been administrated or after the first dose of such compound has been administrated.

6. A method according to claim 1, wherein said aroyl-2H-imidazol-2-on is administered (a) once every four days (b) no more often than weekly (c) less often than once per week (d) each two weeks (e) each three weeks or (f) monthly.

7. A method according to claim 1, wherein said aroyl-2H-imidazol-2- on does not achieve bronchodilatation.

8. A method according to claim 1, wherein the subject shows limited or no response to treatment with at least one of the following: beta-2 agonists, parasympatholytics, anticholinergics, aminophyllines, magnesium sulphate, corticosteroids and cytostatics.

9. A method according to claim 1, wherein said pharmaceutical composition is in a form selected from a tablet; a dispersible tablet; an effervescent tablet; a coated tablet; a delayed release tablet; a modified release tablet; a vaginal tablet in semisolid form; a capsule; a liquid soft gel capsule; a chewing gum; a sublingual preparation; an oral solution; an oral suspension; a powder; an inhalation form; a topical form; a patch; a delayed release patch; a fluid form comprising a compatible dissolving, suspending or emulsifying medium; a cream form comprising a compatible dermatological medium; an enema form; a suppository in semi-solid form; an injectable form; a soap; a shower gel; and a shampoo.

10. A method according to claim 1, wherein the aroyl-2-imidazol-2-on is enoximone.

11. A method according to claim 1, wherein the amount of aroyl-2-H-imidazol-2-on is effective to modulate the immune system involved in the atopic or immune-related disorder in the subject.

12. A method according to claim 2, wherein the asthma is selected from the group consisting of refractory asthma, difficult-to-treat asthma, stable asthma, acute asthma, corticosteroid-resistant asthma, and aggravated asthma as a result of an inflammatory reaction or an allergic reaction.

13. A method according to claim 3, wherein the allergy is any allergic disorder wherein IgE is produced.

14. A method according to claim 12, wherein the allergic disorder wherein IgE is produced is selected from the group consisting of hay fever, allergies to domestic animals, constitutional eczema, food allergies, allergic rhinitis and contact allergies.

15. A method according to claim 1, wherein the disease or condition is COPD.

16. A method according to claim 13, wherein the allergic disorder wherein IgE is produced is selected from the group consisting of hay fever, allergies to domestic animals, constitutional eczema, food allergies, allergic rhinitis and contact allergies.

17. A method for delaying, ameliorating and/or treating asthma, COPD or allergy in a subject, said method comprising administering to the subject a dose from .05 mg/kg to 0.5 mg/kg of an aroyl-2H-imidazol-2-on or a pharmaceutically acceptable salt thereof or a pharmaceutical composition comprising a dose from .05 mg/kg to 0.5 mg/kg an aroyl-2H-imidazol-2-on or a pharmaceutically acceptable salt thereof, wherein said dose is administered no more often than three times per week, wherein an improvement of a parameter or a symptom associated with said disorder has a duration of at least 2 days after a first dose of such compound has been administrated, wherein said symptom associated with said disorder is selected from the group consisting of
  (i) itching, red skin, and urticarial for (domestic) animal allergy, and
  (ii) sneezing, nasal blockage, nasal discharge, itching of the nose, itching of the eye, and itching of the palate, for allergic rhinitis, and
  (iii) difficulty of breathing, wheezing, dyspnea, coughing, chest tightness, sputum production, and nighttime awakenings for asthma, and
  wherein said parameter associated with said disorder is selected from the group consisting of an inhibition of activity of cells of the immune system or a detectable decrease of activity of cells of the immune system, and/or an inhibition of activity or proliferation of T-cells stimulated with an antigen or an allergen or a detectable decrease of activity or of proliferation of such T-cells, and/or an inhibition of activity or proliferation of eosinophils or a detectable decrease of activity or of proliferation of eosinophils, and/or an inhibition of activity or proliferation of ILC2 cells or a detectable decrease of activity or of proliferation of ILC2 cells, and/or an inhibition of activity or proliferation of dendritic cells or a detectable decrease of activity or of proliferation of dendritic cells and/or an inhibition of activity or proliferation of B cells or a detectable decrease of activity or of proliferation of B cells and/or an inhibition of activity or proliferation of macrophages or a detectable decrease of activity or of proliferation of macrophages, and/or a decrease or reduction of the level of IgE.

18. The method of claim 17, wherein said dose is administered orally or by injection.

19. The method of claim 18, wherein said injection is subcutaneous, intracutaneous, intramuscular or intravenous injection.

* * * * *